US008816067B2

(12) United States Patent
Naeye et al.

(10) Patent No.: US 8,816,067 B2
(45) Date of Patent: Aug. 26, 2014

(54) COMPOSITIONS AND METHODS FOR MAKING ALPHA-(1,2)-BRANCHED ALPHA-(1,6) OLIGODEXTRANS

(75) Inventors: Thierry Naeye, Toufflers (FR); Alexandra Einerhand, Alkmaar (NL); Michel Lopez, Nogent sur Seine (FR); Susan M. Potter, Decatur, IL (US); Magali Remaud-Siméon, Ramonville (FR); Pierre Frédéric Emmanuel Monsan, Mondonville (FR)

(73) Assignee: Tate & Lyle Ingredients France SAS, Villeneuve d'Ascq. (FR)

( * ) Notice: Subject to any disclaimer, the term of this patent is extended or adjusted under 35 U.S.C. 154(b) by 430 days.

(21) Appl. No.: 12/775,656

(22) Filed: May 7, 2010

(65) Prior Publication Data

US 2010/0284972 A1    Nov. 11, 2010

Related U.S. Application Data

(60) Provisional application No. 61/176,242, filed on May 7, 2009.

(51) Int. Cl.
 C08B 37/02    (2006.01)
 C07B 37/00    (2006.01)
(52) U.S. Cl.
 CPC ..................... C07B 37/00 (2013.01)
 USPC .................................. 536/123.12
(58) Field of Classification Search
 None
 See application file for complete search history.

(56) References Cited

U.S. PATENT DOCUMENTS

| | | | |
|---|---|---|---|
| 5,141,858 A | 8/1992 | Paul et al. | |
| 2006/0067921 A1 | 3/2006 | Conway | |
| 2006/0100172 A1 | 5/2006 | Monsan et al. | |
| 2006/0210510 A1 | 9/2006 | Bozonnet et al. | |
| 2007/0298080 A1 | 12/2007 | Desreumaux et al. | |

FOREIGN PATENT DOCUMENTS

| | | |
|---|---|---|
| CN | 1690085 | 11/2005 |
| EP | 0 325 872 A1 | 8/1989 |
| FR | 2 822 162 A1 | 9/2002 |
| FR | 2 822 163 A1 | 9/2002 |
| GB | 749515 | 5/1956 |
| JP | 3-503238 | 7/1991 |
| KR | 501584 | 7/2005 |
| WO | WO 02/074943 A2 | 9/2002 |
| WO | WO 2007/091178 A2 | 8/2007 |
| WO | WO 2008/114503 A1 | 9/2008 |
| WO | WO 2009/000803 A1 | 12/2008 |

OTHER PUBLICATIONS

Gomez de Segura, et al., Journal of Biotechnology, 2006, 124, 439-445.*
Dols-Lafargue et al., "Factors Affecting $\alpha$,—1,3 Glucooligosaccharide Synthesis by *Leuconostoc mesenteroides* NRRL B-1299 Dextransucrase," Biotechnology and Bioengineering, vol. 24, No. 6 (2001), pp. 498-504.
Fabre et al., "Role of the Two Catalytic Domains of DSR-E Dextransucrase and Their Involvement in the Formation of Highly $\alpha$-1,2 Branched Dextran," Journal of Bacteriology, vol. 187, No. 1 (2005), pp. 296-303.
Kendall et al., "Effect of Novel Maize-based Dietary Fibers on Postprandial Glycemia and Insulinemia," Journal of the American College of Nutrition, vol. 27, No. 6, (2008), pp. 711-718.
Monchois et al., "Cloning and sequencing of a gene coding for a novel dextransucrase from *Leuconostoc mesenteroides* NRRL B-1299 synthesizing only $\alpha$(1-3) linkages," Gene, vol. 182, No. 1-2 (1996), pp. 23-32.
Remaud-Simeon et al., "Production and Use of Glucosyltransferases from *Leuconostoc mesenteroides* NRRL B-1299 for the Synthesis of Oligosaccharides Containing $\alpha$(1-2) Linkages," Applied Biochemistry and Biotechnology, vol. 44, No. 2 (1994), pp. 101-117.
Jill A. Parnell et al., Weight Loss During Oligofructose Supplementation is Associated with Decreased Ghrelin and Increased Peptide Y in Overweight and Obese adults, American Society for Nutrition, (2009), vol. 89, pp. 1751-1759.
Christel Rousseaux et al., *Lactobacillus acidophilus* Modulates Intestinal Pain and Induces Opioid and Cannabinoid Receptors, Nature Medicine, vol. 13, No. 1, (2007), pp. 35-37.
International Search report for PCT/US2010/033984 dated Jun. 29, 2010.
International Search Report and Written Opinion for Application No. PCT/US2010/033984 Dated Jun. 7, 2010.
International Preliminary Report on Patentability for Application No. PCT/US2010/033984 Dated Jul. 7, 2011.
Marguerite Dols, et al; "Structural Characterization of the Maltose Acceptor-Products Synthesized by *Leuconostoc Mesenteroides* NRRL B-1299 Dextransucrase"; Elsevier Science Ltd., Carbohydrate Research 305 (1998), pp. 549-559.
Mountzouris, et al; "Continuous Production of Oligodextrans Via Controlled Hydrolysis of Dextran in an Enzyme Membrane Reactor"; Journal of Food Science; vol. 67, Nr. 5, 2001; pp. 1767-1771.
First Office Action with Search Report for Chinese Patent Application 201080020234.2, dated Mar. 5, 2013, with English language translation.
Japanese Office Action Issued in Application No. 2012-509997, Dated May 27, 2014.
Maina, et al.; *NMR Spectroscopic Analysis of Exopolysaccharides Produced by Leuconostoc citreum and Weissella confusa*; Carbohydrate Research, 2008, vol. 343, pp. 1446-1455.

* cited by examiner

*Primary Examiner* — Eric S Olson
(74) *Attorney, Agent, or Firm* — RatnerPrestia

(57) ABSTRACT

Compositions for improving the health of a subject comprise alpha-(1,2)-branched alpha-(1,6) oligodextrans, preferably with an average molecular weight between about 10 kDa and 70 kDa, between about 10% and 50% alpha-(1,2)-osidic side chains, and having at least partial indigestibility in the subject. Methods for improving the health of a subject comprise administering the composition to a subject in an amount effective to improve gut health, or to prevent or treat a gastrointestinal disorder, a cholesterol-related disorder, diabetes, or obesity. Methods for making oligodextrans having controlled size and controlled degree of branching comprise providing alpha-(1,6) oligodextrans having an average molecular weight between 0.5 and 100 kDa and introducing at least 10% alpha-(1,2)-osidic side chains onto the alpha-(1,6) oligodextrans.

4 Claims, 16 Drawing Sheets

Mean value of bacterial population (log 10 cells ml$^{-1}$ batch culture fluid) in pH controlled batch cultures at 0, 10, 24, 36 and 48 h:

| Substrate | h | Total cell population | Bifidobacterium | Bacteroides | Lactobacillus |
|---|---|---|---|---|---|
|  | 0 | 9.46 (0.12) | 8.03 (0.14) | 8.48 (0.38) | 7.77 (0.31) |
| Dextran 1 kD | 10 | 9.81 (0.02)* | 9.26 (0.18)** | 9.24 (0.30) | 7.81 (0.29) |
|  | 24 | 9.76 (0.19) | 9.13 (0.22)** | 9.09 (0.36) | 7.59 (0.29) |
|  | 36 | 9.69 (0.19) | 9.26 (0.40)** | 8.74 (0.41) | 7.97 (0.53) |
|  | 48 | 9.56 (0.14) | 8.90 (0.35)** | 8.94 (0.37) | 8.10 (0.47) |
| Dextran 1 kD + 16% α-1,2 | 10 | 9.76 (0.20) | 8.78 (0.15)** | 9.12 (0.46) | 7.80 (0.13) |
|  | 24 | 9.72 (0.29) | 8.72 (0.25)** | 9.19 (0.53) | 7.51 (0.18) |
|  | 36 | 9.67 (0.33) | 8.94 (0.25)** | 8.95 (0.58) | 7.74 (0.23) |
|  | 48 | 9.77 (0.12) | 8.84 (0.21)** | 8.41 (0.39) | 7.86 (0.75) |
| Dextran 1 kD + 32% α-1,2 | 10 | 9.63 (0.33) | 8.67 (0.30)* | 9.12 (0.57) | 7.87 (0.12) |
|  | 24 | 9.77 (0.27) | 8.82 (0.37)** | 9.18 (0.46) | 7.80 (0.63) |
|  | 36 | 9.57 (0.17) | 8.79 (0.16)** | 8.98 (0.47) | 8.62 (0.28) |
|  | 48 | 9.61 (0.24) | 8.58 (0.24) | 8.46 (0.35) | 8.07 (0.59) |
| Dextran 6 kD | 10 | 9.63 (0.15) | 8.14 (0.20) | 9.37 (0.16)** | 8.08 (0.30) |
|  | 24 | 9.87 (0.12) | 8.27 (0.31) | 9.46 (0.12)** | 7.94 (0.30) |
|  | 36 | 9.71 (0.35) | 7.90 (0.18) | 8.82 (0.39) | 8.03 (0.37) |
|  | 48 | 9.79 (0.32) | 8.00 (0.52) | 8.79 (0.31)[b] | 8.14 (0.43) |
| Dextran 6 kD + 33% α-1,2 | 10 | 9.75 (0.31) | 8.04 (0.25) | 8.67 (0.42) | 7.81 (0.19) |
|  | 24 | 9.72 (0.27) | 7.91 (0.05) | 9.07 (0.32) | 7.56 (0.15) |
|  | 36 | 9.80 (0.15) | 7.71 (0.24) | 9.10 (0.52) | 7.62 (0.22) |
|  | 48 | 9.60 (0.17) | 7.81 (0.51) | 8.72 (0.26) | 7.62 (0.34) |
| Dextran 70 kD | 10 | 9.76 (0.11) | 8.53 (0.32) | 9.36 (0.15)* | 7.82 (0.21) |
|  | 24 | 9.65 (0.28) | 8.46 (0.14) | 9.18 (0.33) | 7.56 (0.24) |
|  | 36 | 9.64 (0.32) | 8.65 (0.26) | 8.88 (0.29) | 7.92 (0.44) |
|  | 48 | 9.61 (0.22) | 8.41 (0.55) | 8.45 (0.54)[a] | 7.75 (0.41) |
| Dextran 70 kD + 15% α-1,2 | 10 | 9.60 (0.28) | 8.13 (0.22) | 9.22 (0.36)* | 7.67 (0.13) |
|  | 24 | 9.50 (0.13) | 8.41 (0.53) | 9.19 (0.12) | 7.71 (0.08) |
|  | 36 | 9.80 (0.26) | 8.40 (0.51) | 8.85 (0.31) | 7.82 (0.29) |
|  | 48 | 9.65 (0.38) | 8.29 (0.36) | 8.54 (0.41) | 7.77 (0.54) |
| Dextran 70 kD + 37% α-1,2 | 10 | 9.41 (0.24) | 8.05 (0.24) | 8.83 (0.45) | 7.64 (0.16) |
|  | 24 | 9.57 (0.22) | 8.12 (0.29) | 9.02 (0.56) | 7.60 (0.11) |
|  | 36 | 9.57 (0.27) | 7.83 (0.23) | 8.78 (0.64) | 7.54 (0.24) |
|  | 48 | 9.52 (0.31) | 7.94 (0.23) | 8.45 (0.31) | 7.79 (0.11) |

Univariate ANOVA and Tukey's test were used to determine significant increase/decrease of bacterial populations within each treatment.
*Significant difference from 0 h value, $P < 0.05$.
**Significant difference from 0 h value, $P < 0.01$.
[a]Significant difference from 10 h value, $P < 0.05$.
[b]Significant difference from 24 h , $P < 0.01$.
[c]Percent of the microbial communities diversity enumerated by the probe set compared with DAPI. Standard deviation is shown in parentheses (n=4).

FIG. 1-1

| Substrate | Clostridium | Atopobium | Eubacterium | Clostridium Cluster IX |
|---|---|---|---|---|
| | 7.55 (0.51) | 8.15 (0.45) | 8.53 (0.17) | 8.41 (0.29) |
| Dextran 1 kD | 7.47 (0.33) | 8.24 (0.30) | 8.17 (0.33) | 8.45 (0.30) |
| | 7.44 (0.34) | 8.31 (0.50) | 8.42 (0.18) | 8.42 (0.19) |
| | 7.50 (0.26) | 8.45 (0.17) | 8.24 (0.13) | 8.34 (0.16) |
| | 7.25 (0.10) | 8.49 (0.23) | 8.25 (0.24) | 7.95 (0.39) |
| Dextran 1 kD + 16% α-1,2 | 7.53 (0.22) | 8.36 (0.52) | 8.30 (0.38) | 8.25 (0.30) |
| | 7.32 (0.14) | 8.30 (0.57) | 8.38 (0.48) | 8.59 (0.06) |
| | 7.61 (0.24) | 8.44 (0.44) | 8.36 (0.20) | 8.12 (0.27) |
| | 7.16 (0.12) | 8.35 (0.44) | 8.57 (0.04) | 8.10 (0.49) |
| Dextran 1 kD + 32% α-1,2 | 7.49 (0.21) | 8.25 (0.23) | 8.33 (0.33) | 8.57 (0.18) |
| | 7.49 (0.30) | 8.30 (0.66) | 8.52 (0.29) | 8.42 (0.27) |
| | 7.52 (0.33) | 8.32 (0.47) | 8.48 (0.31) | 8.25 (0.15) |
| | 7.39 (0.21) | 8.15 (0.47) | 8.51 (0.19) | 7.83 (0.43)[a] |
| Dextran 6 kD | 7.57 (0.20) | 8.46 (0.52) | 8.20 (0.28) | 8.46 (0.20) |
| | 7.53 (0.30) | 8.53 (0.31) | 8.49 (0.13) | 8.62 (0.32) |
| | 7.80 (0.78) | 8.63 (0.12) | 8.74 (0.17)[a] | 8.24 (0.28) |
| | 7.48 (0.13) | 8.47 (0.45) | 8.39 (0.18) | 8.01 (0.40) |
| Dextran 6 kD + 33% α-1,2 | 7.52 (0.30) | 8.21 (0.30) | 8.36 (0.18) | 8.57 (0.20) |
| | 7.36 (0.31) | 8.22 (0.23) | 8.53 (0.21) | 8.47 (0.37) |
| | 7.68 (0.37) | 8.18 (0.13) | 8.24 (0.32) | 8.16 (0.28) |
| | 7.28 (0.30) | 8.27 (0.50) | 8.21 (0.25) | 8.00 (0.51) |
| Dextran 70 kD | 7.68 (0.33) | 8.45 (0.30) | 8.52 (0.21) | 8.34 (0.27) |
| | 7.34 (0.20) | 8.36 (0.32) | 8.42 (0.11) | 8.44 (0.34) |
| | 7.58 (0.48) | 8.54 (0.31) | 8.28 (0.36) | 8.10 (0.19) |
| | 7.38 (0.26) | 8.37 (0.37) | 8.38 (0.31) | 7.84 (0.21)[b] |
| Dextran 70 kD + 15% α-1,2 | 7.57 (0.26) | 8.30 (0.29) | 8.36 (0.16) | 8.54 (0.33) |
| | 7.48 (0.32) | 8.18 (0.27) | 8.23 (0.17) | 8.35 (0.49) |
| | 7.52 (0.53) | 8.36 (0.36) | 8.26 (0.23) | 8.10 (0.32) |
| | 7.38 (0.15) | 8.27 (0.38) | 8.33 (0.25) | 8.00 (0.30) |
| Dextran 70 kD + 37% α-1,2 | 7.72 (0.43) | 8.16 (0.16) | 8.25 (0.09) | 8.44 (0.22) |
| | 7.43 (0.42) | 8.33 (0.23) | 8.22 (0.19) | 8.51 (0.41) |
| | 7.54 (0.51) | 8.15 (0.37) | 8.33 (0.20) | 8.31 (0.44) |
| | 7.30 (0.09) | 8.33 (0.17) | 8.34 (0.16) | 7.96 (0.28) |

FIG. 1-2

Mean value of SCFA and lactic acid concentration (mM) in pH controlled batch cultures at 0, 10, 24, 36 and 48 h:

| Substrate | Time (h) | Lactate | | Acetate | | Propionate | |
|---|---|---|---|---|---|---|---|
| | 0 | 0.00 | (0.00) | 0.00 | (0.00) | 0.00 | (0.00) |
| Dextran 1 kD | 10 | 8.98 | (4.65)** | 45.13 | (14.25)** | 7.70 | (5.04) |
| | 24 | 0.00 | (0.00)ᵃᵃ | 57.67 | (6.13)** | 15.04 | (5.12) |
| | 36 | 0.00 | (0.00)ᵃᵃ | 53.35 | (6.86)** | 19.26 | (5.87) |
| | 48 | 0.00 | (0.00)ᵃᵃ | 59.46 | (6.76)** | 16.44 | (4.84) |
| Dextran 1 kD + 16% α-1,2 | 10 | 0.10 | (0.30) | 36.08 | (24.71) | 10.90 | (6.21) |
| | 24 | 0.00 | (0.00) | 36.77 | (16.81)** | 20.56 | (8.75) |
| | 36 | 0.00 | (0.00) | 52.67 | (13.03)** | 22.60 | (7.20) |
| | 48 | 0.00 | (0.00) | 47.96 | (0.57)** | 26.48 | (2.61)* |
| Dextran 1 kD + 32% α-1,2 | 10 | 0.60 | (1.19) | 20.66 | (11.60)** | 9.09 | (6.53) |
| | 24 | 0.00 | (0.00) | 42.45 | (5.60)ᵃᵃ | 28.66 | (3.40) |
| | 36 | 0.00 | (0.00) | 41.97 | (5.47)ᵃᵃ | 28.75 | (4.52) |
| | 48 | 0.00 | (0.00) | 43.11 | (5.87)ᵃᵃ | 30.65 | (3.71)ᵃ |
| Dextran 6 kD | 10 | 0.57 | (1.14) | 15.30 | (3.44)**ᵃᵃ | 7.75 | (3.60)* |
| | 24 | 0.00 | (0.00) | 35.04 | (5.60)ᵃ | 27.74 | (6.63)ᵃᵃ |
| | 36 | 0.00 | (0.00) | 38.27 | (11.61)ᵃ | 31.21 | (4.27)ᵃᵃ |
| | 48 | 0.00 | (0.00) | 37.59 | (12.65)ᵃ | 28.46 | (6.23)ᵃᵃ |
| Dextran 6 kD + 33% α-1,2 | 10 | 0.00 | (0.00) | 12.90 | (10.21) | 7.62 | (5.75) |
| | 24 | 0.26 | (0.53) | 32.44 | (7.33)ᵃ | 25.09 | (2.74)ᵃᵃ |
| | 36 | 0.00 | (0.00) | 35.57 | (8.92)ᵃᵃ | 26.11 | (4.40)ᵃᵃ |
| | 48 | 0.00 | (0.00) | 35.70 | (6.38)ᵃᵃ | 28.60 | (2.43)ᵃᵃ |
| Dextran 70 kD | 10 | 0.30 | (0.50) | 23.43 | (11.71)** | 12.59 | (5.79)* |
| | 24 | 0.33 | (0.66) | 37.86 | (8.06)** | 25.07 | (9.06)* |
| | 36 | 0.00 | (0.00) | 35.59 | (3.94)** | 27.17 | (9.91)* |
| | 48 | 0.00 | (0.00) | 38.13 | (10.17)** | 26.62 | (9.76) |
| Dextran 70 kD + 15% α-1,2 | 10 | 0.00 | (0.00) | 15.58 | (6.86) | 8.35 | (2.86)* |
| | 24 | 0.00 | (0.00) | 40.17 | (10.95)ᵃ | 27.60 | (1.69)ᵃᵃ |
| | 36 | 0.00 | (0.00) | 39.93 | (12.50)ᵃ | 29.29 | (1.85)ᵃᵃ |
| | 48 | 0.00 | (0.00) | 42.51 | (15.21)ᵃ | 30.68 | (3.28)ᵃᵃ |
| Dextran 70 kD + 37% α-1,2 | 10 | 0.54 | (1.08) | 8.44 | (2.19) | 4.55 | (3.00) |
| | 24 | 2.15 | (2.69) | 30.70 | (6.25)ᵃ | 25.37 | (12.78)ᵃ |
| | 36 | 1.14 | (2.28) | 30.14 | (7.55)ᵃ | 29.12 | (6.45)ᵃᵃ |
| | 48 | 0.60 | (1.21) | 29.88 | (8.40)ᵃ | 28.38 | (6.93)ᵃᵃ |
| Inulin TEX | 10 | 5.16 | (5.12) | 25.27 | (8.97)** | 10.97 | (5.26)* |
| | 24 | 1.24 | (2.47) | 34.59 | (3.96)** | 18.76 | (7.72)* |
| | 36 | 0.40 | (0.80) | 35.43 | (3.83)** | 19.74 | (7.44)* |
| | 48 | 0.00 | (0.00) | 36.97 | (5.78)** | 19.57 | (7.12)* |

Univariate ANOVA and Tukey's test were used to determine significant increase/decrease in each SCFA concentrations within each treatment.
*Significant difference from 0 h value, $P < 0.05$.
**Significant difference from 0 h value, $P < 0.01$.
ᵃSignificant difference from 10 h value, $P < 0.05$.
ᵃᵃSignificant difference from 10 h value, $P < 0.01$. Standard deviation is shown in parentheses (n=4).

FIG. 2-1

| Substrate | Butyrate | | Total SCFA | |
|---|---|---|---|---|
| | 0.00 | (0.00) | 0.00 | (0.00) |
| Dextran 1 kD | 0.59 | (1.18) | 53.42 | (19.74)** |
| | 3.71 | (1.00)aa | 76.41 | (10.01) |
| | 5.10 | (1.69)aa | 77.70 | (9.09) |
| | 4.65 | (0.79)aa | 80.56 | (9.35)aa |
| Dextran 1 kD + 16% α-1,2 | 2.65 | (2.29)* | 30.03 | (25.51) |
| | 2.66 | (1.71) | 59.98 | (26.57)** |
| | 3.40 | (1.14) | 59.00 | (39.74)**a |
| | 3.75 | (1.27) | 58.64 | (39.12)**a |
| Dextran 1 kD + 32% α-1,2 | 1.25 | (1.58)* | 31.00 | (19.56)** |
| | 4.20 | (1.37)* | 75.31 | (4.09)**aa |
| | 4.92 | (1.39)a | 75.63 | (1.06)aa |
| | 5.72 | (3.14) | 79.48 | (2.90)**aa |
| Dextran 6 kD | 1.50 | (0.56) | 24.55 | (5.58)** |
| | 6.01 | (0.84)aa | 68.79 | (4.31)aa |
| | 8.86 | (1.73)aa | 78.34 | (10.93)aa |
| | 9.16 | (3.13)aa | 75.21 | (6.76)aa |
| Dextran 6 kD + 33% α-1,2 | 1.05 | (2.10) | 21.57 | (18.01) |
| | 3.95 | (2.31)* | 61.48 | (6.76)**aa |
| | 5.33 | (1.78)a | 67.00 | (6.45)aa |
| | 5.77 | (1.72)a | 70.07 | (6.07)aa |
| Dextran 70 kD | 2.27 | (1.87) | 38.29 | (17.93)** |
| | 4.79 | (0.74) | 67.72 | (11.64)**a |
| | 6.42 | (1.40) | 69.18 | (11.83)**a |
| | 6.51 | (1.19) | 71.27 | (15.84)**a |
| Dextran 70 kD + 15% α-1,2 | 1.26 | (1.60) | 25.18 | (10.56)** |
| | 4.55 | (2.05) | 72.31 | (11.44)**aa |
| | 5.18 | (2.51)* | 74.40 | (15.56)**aa |
| | 5.95 | (2.99)a | 79.13 | (20.60)aa |
| Dextran 70 kD + 37% α-1,2 | 0.00 | (0.00) | 12.99 | (5.16) |
| | 2.51 | (1.75)*a | 58.57 | (19.23)**aa |
| | 3.02 | (1.47)aa | 62.28 | (13.31)aa |
| | 3.75 | (0.70)aa | 62.01 | (13.86)aa |
| Inulin TEX | 5.33 | (6.96) | 41.57 | (16.10)** |
| | 8.30 | (5.12) | 61.65 | (3.92)**aa |
| | 8.49 | (4.29) | 63.66 | (2.03)**aa |
| | 8.25 | (3.32) | 67.80 | (1.84)**aa |

FROM FIG. 2-1

FIG. 2-2

Acetate to propionate ratio (mM) in pH controlled batch culture fermentation using respective substrate (n=4)

Total gas production (ml) after 36 h non-pH controlled batch culture fermentation using respective substrate (n=4). Univariate ANOVA and Tukey's test were used to determine significant differences (P < 0.05) among treatment as indicated with different letters above bars.

Evaluation of the effect of oligodextrans on microflora

| Treatment | Enterococci | Enterobacteria | Lactobacilli | Total germs |
|---|---|---|---|---|
| Vehicle(drinking water) | 7.51±0.36 | 6.55±0.66 | 8.74±0.38 | 9.05±0.41 |
| DEX-1000-15 (1%) F1-1% | 7.36±0.18 | 5.88±0.9 | 9.09±0.45 | 9.65±0.06 |
| DEX-1000-15 (5%) F1-5% | 7.18±0.28 | 6.49±0.8 | 9.22±0.41 | 9.33±0.37 |
| DEX-1000-30 (1%) F2-1% | 7.27±0.44 | 5.85±0.52 | 9.32±0.3 | 9.64±0.4 |
| DEX-1000-30 (5%) F2-5% | 7.05±0.29 | 6.56±0.7 | 9.47±0.2 | 9.41±0.27 |
| DEX-7000-30 (1%) F3-1% | 7.16±0.37 | 6.16±0.58 | 9.33±0.25 | 9.59±0.48 |
| DEX-7000-30 (1%) F3-5% | 6.94±0.34 | 5.74±0.29 | 9.29±0.38 | 9.05±0.41 |

FIG. 7

Sample R3: Sucrose + glucansucrase DSR S
Presence of numerous peaks in the sample (R3) between the pure α 1,6 structures of the commercial DEX1000.

Sample R4: Sucrose 272g/kg + Glucose 27g/kg
Adding the glucose helps clearly to get pure α 1,6 structures.

Production of alpha 1,6 backbone by glucan sucrases in presence of different ratio of sucrose/glucose

|    | Sucrose g/Kg | Glucose g/Kg | D/A |
|----|--------------|--------------|-----|
| R4 | 272          | 27           | 10  |
| M3 | 308.5        | 51.5         | 6   |
| M1 | 240          | 120          | 2   |

At D/A (donor/acceptor) =10 the DP are much higher than in the ref. DEX1000 commercial. Lowering D/A down to 6 and then to 2 clearly limits the synthesis of high DP.

Example of synthesis of controlled size backbone (DEX500 and DEX1000) with the DSR-S glucan sucrase.

|         | Sucrose g/Kg | Glucoseg/Kg | D/A |
|---------|--------------|-------------|-----|
| DEX500  | 240          | 120         | 2   |
| DEX1000 | 195          | 335.5       | 0.6 |

HPAEC PAD chromatograms of DEX1000 centered on IM4-IM5 with no high DP

| group | Body weight gain | | Fasting glucose mg/dl |
|---|---|---|---|
| | Body weight gain (g) | Body weight gain (% of day 1) | |
| Ctrl DIO D12492 | 8,00 ± 1,44 | 37,81% ± 6,83% | 128,63 ± 19,86 |
| DIO D12492 + TLD 1015 | 7,28 ± 1,83 | 34,08% ± 7,25% | 103,25 ± 15,89* |
| DIO D12492 + TLD 1030 | 5,88 ± 1,09** | 28,12% ± 6,12%** | 115,63 ± 23,35 |
| DIO D12492 + TLD 7030 | 6,51 ± 2,30 | 30,94% ± 11,61% | 117,75 ± 25,16 |

FIG. 11

COMPOSITIONS AND METHODS FOR MAKING ALPHA-(1,2)-BRANCHED ALPHA-(1,6) OLIGODEXTRANS

CROSS-REFERENCE TO RELATED APPLICATIONS

This application claims priority to application Ser. No. 61/176,242, filed May 7, 2009, which is incorporated herein by reference in its entirety for all purposes.

FIELD OF THE INVENTION

The present invention relates to alpha-(1,2)-branched alpha-(1,6) oligodextrans. In particular, embodiments of the present invention relate to compositions and methods for improving the gastrointestinal and cardiovascular health of a subject using alpha-(1,2)-branched alpha-(1,6) oligodextrans.

BACKGROUND OF THE INVENTION

Prebiotics, such as oligosaccharides, are non-digestible dietary compounds broken down by the micro-organisms of the intestinal flora. The breakdown of prebiotics often exerts beneficial effects on the health of the host. These beneficial health effects are due to a selective stimulation of the growth and/or biological activity of a limited number of microbial genera, species, or strains in the gut microbiota that confer health benefits to the host, in particular the bifidobacteria and the lactic acid bacteria of the gut flora. Prebiotics have been shown to increase fecal and mucosal bifidobacteria in healthy subjects. Oligosaccharides are widely used in foods such as soft drinks, cookies, cereals, candies, and dairy products. Other applications for oligosaccharides such as an anti-cariogenic agent or a low sweetness humectant have also been explored.

The effects of prebiotics are principally due to selective stimulation of the growth of bifidobacteria (also known as a bifidogenic effect) and/or other beneficial bacteria in the gut. The stimulation of this growth allows a reduction in the pH of the colon, an increase in the production of short chain fatty acids, a prevention of the proliferation and adhesion of pathogenic microorganisms (barrier effect), an increase in the metabolization of potentially carcinogenic aminated compounds, and the production of vitamin B. A disadvantage of oligosaccharides nevertheless is that if they increase carbohydrate fermentation, they also increase gas formation. This means that the main side effects are flatulence, discomfort, and bloating.

Currently, the most clearly defined prebiotics are carbohydrates classed among dietary fibers: non-digestible oligosaccharides (also called oligosides). Oligosaccharides have a low degree of polymerization. The saccharide units involved in the formation of oligosaccharides are varied. Examples include hexoses, such as glucose, galactose, and fructose, and pentoses, such as xylose. Oligosaccharides may comprise a single type of monosaccharide (homo-oligosides) or a mixture (hetero-oligosides). Oligosaccharides are currently produced from the breakdown of natural polymers such as starch or inulin, from direct extractions out of natural substances, such as soybean, or from chemical or enzymatic syntheses.

The effects of specific prebiotics on many types of health problems are unknown. In the context of an unbalanced diet, broad sections of the population display an elevated content of blood fat values, in particular blood cholesterol values. High cholesterol levels are considered principal risk factors for cardiovascular disorders. Therefore, therapeutic treatments for significantly increased cholesterol values, in particular LDL cholesterol, and increased blood fat values, are urgently necessary. Various approaches to a solution have been described for this; however, the effects of specific prebiotic oligosaccharides on such cholesterol-related diseases or problems are not known. The effects of specific prebiotics on visceral pain and obesity (e.g., fat metabolism), which are problems that also have significant effects on broad sections of the population, are also unknown.

SUMMARY OF THE INVENTION

The present invention provides compositions for improving the health of a subject comprising alpha-(1,2)-branched alpha-(1,6) oligodextrans. The alpha-(1,2)-branched alpha-(1,6) oligodextrans have controlled size and controlled degree of branching. For example, in an embodiment of the present invention the alpha-(1,2)-branched alpha-(1,6) oligodextran has an average molecular weight between about 10 kilodaltons (kDa) and 70 kDa and comprises between about 10% and 50% alpha-(1,2)-osidic side chains.

The present invention also provides methods for improving the health of a subject comprising administering a composition comprising an alpha-(1,2)-branched alpha-(1,6) oligodextran to a subject in an amount effective to exert a beneficial effect on the health of the subject. Beneficial effects may include, for example, improving gut health, improving intestinal comfort, reducing lipid content, affecting weight, or preventing or treating a gastrointestinal disorder, diabetes, obesity, or a cholesterol-related disorder.

The present invention also provides methods for making an oligodextran having controlled size and controlled degree of branching. For example, in an embodiment of the present invention, a method comprises (1) providing an alpha-(1,6) oligodextran having a number average molecular weight between 0.5 and 100 kDa; (2) introducing at least 10% alpha-(1,2)-osidic side chains onto the alpha-(1,6) oligodextran, whereby an alpha-(1,2)-branched alpha-(1,6) oligodextran is obtained; and (3) optionally purifying the alpha-(1,2)-branched alpha-(1,6) oligodextran.

It is to be understood that both the foregoing general description and the following detailed description are exemplary, but not restrictive, of the invention.

BRIEF DESCRIPTION OF THE FIGURES

FIG. 1 illustrates average bacterial counts ($Log_{10}$ cells/ml culture fluid) from 4 healthy donors for *Bifidobacterium, Bacteroides, Lactobacillus, Clostridium, Atopobium, Eubacterium* and *Clostridium* Cluster IX levels for various embodiments of compounds according to the invention at 0, 10, 24, 36 and 48 h of pH controlled fecal batch culture fermentation.

FIG. 2 illustrates short chain fatty acid (SCFA) measurements (mM), in particular lactate, acetate, propionate, and butyrate after administration of various embodiments of compounds according to the invention at 10, 24, 36 and 48 h of pH controlled fecal batch culture fermentation.

FIG. 7 illustrates the effect of compounds according to the present invention on intestinal microflora of rats.

FIG. 11 illustrates body weight gain in rats on a high fat diet following administration of compounds according to the present invention.

DETAILED DESCRIPTION OF THE INVENTION

Figure 3:
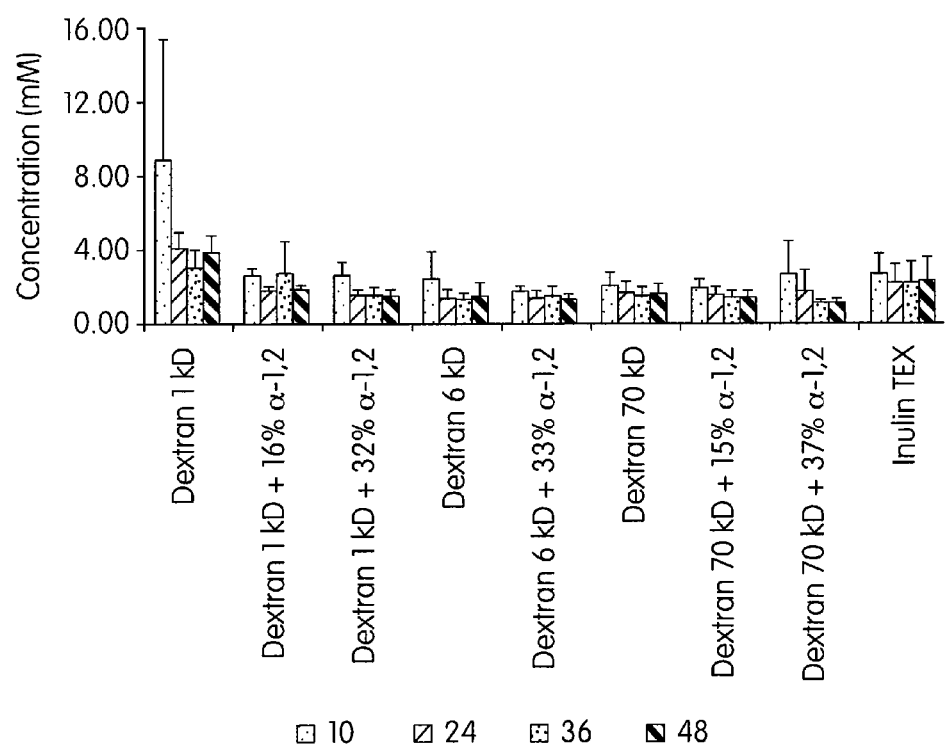
FIG. 3 illustrates acetate to propionate ratios (mM) in pH controlled batch culture fermentation of various embodiments of compounds according to the invention.

The present invention provides branched oligodextran compounds and compositions comprising such compounds. The invention further provides methods for improving the health of a subject comprising administering an oligodextran compound to a subject in an amount effective to exert a beneficial effect on the health of the subject, particularly for improving gastrointestinal health and controlling blood cholesterol levels. The present invention also provides methods for making an oligodextran having controlled size and controlled degree of branching.

A "dextran" is a polymer comprising glucose units, also referred to as a polyglucose, and contains at least 50% of continuous alpha 1,6 glucosidic bonds. Dextrans of a wide variety of structures and molecular weights have been known for many years. Dextrans are produced by lactic acid bacteria growing on a sucrose substrate; for example *Leuconostoc, Lactococcus, Streptococcus, Weisella*, and *Lactobacillus*. The enzymes involved in their synthesis are glucansucrases which produce glucans and release fructose from sucrose substrates. The terms dextran, native dextran and high molecular weight dextran as used herein are synonyms. Dextran often has an average molecular weight above 1000 kDa.

With "oligodextran" or "alpha-(1,6) oligodextran" as used herein is meant a polyglucose with a number average molecular weight ranging between the average molecular weight of an oligoglucoside, which is often below 3 glucose units, and of native dextran which is often above 1000 kDa.

With "alpha-(1,2)-branched alpha-(1,6) oligodextran" as used herein is meant an oligodextran comprising a substantially linear backbone of alpha-D-glucopyranosyl units substantially linked by alpha-(1,6)-linkages and having alpha-(1,2)-osidic side chains. The substantially linear backbone of alpha-D-glucopyranosyl units substantially linked by alpha-(1,6)-linkages is often referred to herein as a "backbone" or "acceptor."

It shall be noted that the terms "glucose" and "glucopyranose" as used herein are considered as synonyms and used interchangeably. Similarly the terms "glucosyl" and "glucopyranosyl" units are used herein are considered as synonyms and used interchangeably.

The term "isomaltooligosaccharides" or IMOS as used herein refers to a compound comprised of glucose monomers linked by alpha-1,6 glucosidic linkages, which can be produced commercially from an enzymatic reaction of alpha-amylase, pullulanase, and beta amylase, alpha-glucosidase upon corn starch or starch derivative products. Commercially available products comprise a mixture of isomaltooligosaccharides (DP ranging from 2 to 8, e.g., isomaltose, isomaltotriose, isomaltotetraose, isomaltopentaose, isomaltohexaose, isomaltoheptaose, isomaltooctaose) and of glucose and of glucooligosaccharides containing both alpha 1-4 and 1-6 linkages (e.g., panose).

With "average molecular weight" it is meant the ordinary arithmetic mean or average of the molecular weights of the individual macromolecules. It is determined by measuring the molecular weight of n polymer molecules, summing the weights, and dividing by n. The number average molecular weight is a way of determining the molecular weight of a polymer. The number average molecular weight of a polymer can be determined by gel permeation chromatography, viscometry and colligative methods such as vapor pressure osmometry or end-group titration.

A "controlled molecular weight" as referred to herein indicates that according to the invention the length, and hence the molecular mass or molecular weight, of the oligodextran compounds can be adjusted or controlled. With "degree of branching" it is meant the number of glucose units in the backbone bearing or coupled to a glucose unit in an alpha-(1,2)-position over the total number of glucose units present in the molecule, expressed in percentage. Thus, the branching degree refers to the percentage of glucose units in an alpha-(1,2)-position over the entire molecule, and not just over the backbone. A "controlled degree of branching" means that this number of glucose units can be adjusted or controlled, according to methods of the present invention.

The term "compound of the invention", "branched oligodextran," and "alpha-(1,2)-branched alpha-(1,6) oligodextran" are used as synonyms herein. In a particular embodiment, the invention relates to alpha-(1,2)-branched alpha-(1,6) oligodextran. In a preferred embodiment, such alpha-(1,2)-branched alpha-(1,6) oligodextran is an alpha-(1,2)-branched alpha-(1,6) oligodextran comprising a linear or substantially linear backbone of alpha-D-glucopyranosyl units substantially linked by alpha-(1,6)-linkages and having alpha-(1,2)-osidic side chains, preferably chains of one or more glucose units.

In a preferred embodiment, the invention relates to oligodextran compounds wherein the alpha-(1,2)-osidic side chains comprise one, two, or three glucose units, preferably one glucose unit. In an example, a single glucose unit is attached to the backbone of the oligodextran to form a branched compound. The term "alpha-(1,2)-osidic side chains" in this context preferably refers to chains of one or more glucose unit(s) that are linked by an alpha-(1,2)-linkage to a glucose unit of the linear backbone.

As described in more detail below, one aspect of the present invention provides compositions for improving the health of a subject comprising an alpha-(1,2)-branched alpha-(1,6) oligodextran. In one embodiment, the oligodextran is a prebiotic compound. An oligodextran according to the present invention preferably comprises at least 10% alpha-(1,2)-osidic side chains and a substantially linear backbone comprising at least two alpha-D-glucopyranosyl units linked by alpha-(1,6)-linkages. The substantially linear backbone preferably comprises at least 90% alpha-(1,6)-D-glucopyranosidic linkages. The backbone comprising alpha-(1,6)-linkages preferably comprises between about 10% and 50% alpha-(1,2)-osidic side chains, and less than 10% alpha-(1,4)-linkages. There are preferably more than one alpha-(1,2)-osidic side chain per molecule. The addition of alpha-(1,2)-osidic side chains onto these backbones increases the average molecular weight according to the degree of branching.

The alpha-(1,2)-osidic side chains may be randomly distributed over the backbone of the oligodextran of the invention or they may be provided on certain areas of the backbone, e.g. at the extremities of the backbone. In a preferred embodiment, the alpha-(1,2)-osidic side chains are randomly distributed over the backbone of an oligodextran.

Preferably, a branched oligodextran according to the invention has an average molecular weight ranging between the average molecular weight of an oligoglucoside, which is generally below 1 kDa, and the average molecular weight of native dextran which is generally above 1000 kDa. For instance, a backbone comprising alpha-(1,6)-linkages preferably has an average molecular weight between 0.5 kDa and 100 kDa, or between 1 kDa and 70 kDa, or between 1 kDa and 10 kDa. In a preferred embodiment, a backbone has an average molecular weight of at least 0.5 kDa, or at least 1 kDa, or at least 10 kDa, or at least 40 kD, or at least 70 kDa. The average molecular weight of an alpha-(1,2)-branched alpha-(1,6) oligodextran according to the invention increases due to the addition of alpha-(1-2) linked residues. Thus, the change in molecular weight is directly linked to the degree of branching and the total number of units (e.g., glucose units) present in the side chains. For example, a range of average molecular weights of the backbone is about 0.5 kDa to about 100 kDa, and a range of average molecular weights of the alpha-(1,2)-branched alpha-(1,6) oligodextran is about 0.60 kDa (e.g., backbone of about 0.5 kDa with 10% branching) to about 170 kDa (e.g., backbone of about 100 kDa with about 40% branching). Other preferred examples of alpha-(1,2)-branched alpha-(1,6) oligodextran compounds according to the invention are provided in the example section.

In a preferred embodiment, an alpha-(1,2)-branched alpha-(1,6) oligodextran according to the invention has more than one alpha-(1,2)-osidic side chain, and a degree of branching of at least 10% alpha-(1,2)-osidic side chains, for instance at least 15%, or at least 20%, or at least 25%, or at least 30%, or at least 35%, or at least 40% alpha-(1,2)-osidic side chains. More preferably, the branching level is between about 10% and 40%, and most preferably about 15%, 16%, 18%, 31%, 32%, 33% or 37%.

In another preferred embodiment, the alpha-(1,2)-branched alpha-(1,6) oligodextran according to the invention comprises less than 10%, preferably less than 5%, alpha-(1,4)-linkages, and more preferably is substantially free of alpha-(1,4)-linkages. An advantage of this is that compounds according to the invention have a low content of easily hydrolyzable bonds. The compound therefore is not highly digestible and is capable of reaching the lower intestine fairly intact so that it can have a maximum impact on the local microflora.

In yet another embodiment, the backbone of the branched oligodextran comprises at least three, and for instance at least four, at least five, or at least six alpha-D-glucopyranosyl units substantially linked by alpha-(1,6)-linkages. In another embodiment, the backbone comprises between six and twelve or between six and ten alpha-D-glucopyranosyl units. In another embodiment the backbone of the oligodextran comprises between 100 and 1000 alpha-D-glucopyranosyl units.

The oligodextran compounds of the present invention comprise a linear or substantially linear backbone of alpha-D-glucopyranosyl units substantially linked by alpha-(1,6)-linkages and having alpha-(1,2)-osidic side chains. The term "substantially linked by alpha-(1,6)-linkages" indicates that most of the glucose units in the linear backbone are linked to one another by alpha-(1,6)-linkages.

In a preferred embodiment, at least 90%; at least 92%; at least 95%; or even at least 97% of the glucose units in the linear backbone of the compound are linked to one another in the linear backbone by alpha-(1,6)-linkages. Therefore, in another embodiment, the oligodextran comprises a linear backbone having at least 90%; at least 92%; at least 95%; or even at least 97% alpha-(1,6)-glucopyranosidic linkages. The invention also provides a branched oligodextran compound wherein the linear backbone comprises less than 10% or less than 5% alpha-(1,4)-linkages of glucose units to one another in the linear backbone.

In a preferred embodiment, the oligodextran backbone comprises at least two alpha-D-glucopyranosyl units substantially linked by alpha-D(1,6)-linkages, preferably between 3 and 600 alpha-D-glucopyranosyl units, and more preferably from 6 to 10 units. In another embodiment, the linear backbone comprises at least 90% alpha-(1,6)-glucopyranosidic linkages.

In another aspect, the invention provides a method for making the compounds described above, preferably of controlled size and of controlled degree of branching. Applicants have discovered a method of synthesis of alpha-(1,2)-branched alpha-(1,6) oligodextrans having a targeted molecular weight and degree of branching. According to this method, a broad range of oligodextran compounds with ranges of molecular weights and degrees of branching can be prepared. In particular, applicants have established a way to graft alpha-(1,2)-branches onto a backbone comprising glucose units. The backbone comprising glucose units is preferably a linear or substantially linear oligodextran whereby the average molecular weight ranges between 0.5 and 70 kDa.

Therefore, another aspect of the invention provides a method for preparing alpha-(1,2)-branched alpha-(1,6) oligodextrans comprising the steps of providing oligosaccharides, preferably an oligodextran, of a suitable molecular weight, and introducing alpha-(1,2)-osidic side chains onto the oligodextran. Optionally the method comprises a purification step for removing unwanted co-products, such as, for example, fructose, glucose, leucrose, kojibiose, and/or residual sucrose, that have been obtained during the preparation method.

In a preferred embodiment, a method as described above for making an oligodextran having controlled size and controlled degree of branching comprises the steps of (1) providing an alpha-(1,6) oligodextran having an average molecular weight between 0.5 and 100 kDa; (2) introducing at least 10% alpha-(1,2)-osidic side chains onto the alpha-(1,6) oligodextran obtained in step (1), whereby an alpha-(1,2)-branched alpha-(1,6) oligodextran is obtained; and (3) optionally purifying the alpha-(1,2)-branched alpha-(1,6) oligodextran to remove unwanted co-products that have been obtained during the method.

In a preferred embodiment, step (1) comprises (1a) subjecting a glucose-containing starting material to an enzymatic transglucosylation reaction whereby isomaltooligosaccharides (IMOS) are obtained; and (1b) reacting the IMOS with a glucan sucrase in the presence of sucrose whereby alpha-(1,6) oligodextran is obtained. In one embodiment, (1a) and (1b) are performed in a single step. The glucose-containing starting material may comprise, for example, dextran, starch, glucose syrup, dextrose, or maltose syrup.

In general, IMOS are enzymatically produced by transglucosylation of maltose syrup as substrate. The maltose syrups can be made using alpha-amylase, pullulanase, beta-amylase, and/or alpha-glucosidase as catalysts. Consequently, according to the present invention, the IMOS obtained by transglucosylation can be directly used without any purification process. On the other hand, other alpha-(1-6) oligodextrans are typically produced by partial hydrolysis and fractionation of high molecular weight dextrans from sucrose substrate. Prior to branching, these products must be purified to eliminate fructose residues.

An oligodextran provided in step (1) preferably has a linear or substantially linear backbone. More preferably, the oligodextran has a glycosidic backbone comprising at least 90% alpha-(1,6)-D-glucopyranosidic linkages, more preferably at least 92%, 95%, or 97% alpha-(1,6)-D-glucopyranosidic linkages.

In another embodiment, the oligodextran provided in step (1) has a molecular weight between 0.5 and 100 kDa; for instance, between 1 and 70 kDa, or between 1 and 40 kDa. In yet another embodiment, the oligodextran provided by step (1) has an average molecular weight between 0.5 and 10 kDa. In still another embodiment, the oligodextran provided by step (1) has an average molecular weight of at least 0.5 kDa or at least 1 kDa or at least 70 kD. The average molecular weight of the oligodextran provided by step (2) increases due to the addition of alpha-(1-2) linked residues. Thus, the change in molecular weight is directly linked to the degree of branching and the total number of units (e.g., glucose units) present in the side chains. For example, a range of average molecular weights of the backbone produced in step (1) is about 0.5 kDa to about 100 kDa, and a range of average molecular weights of the alpha 1,2 alpha 1,6 oligodextrans is about 0.60 kDa to about 170 kDa.

Oligodextrans provided in step (1) can be prepared from different starting materials. In one embodiment, an oligodextran provided in step (1) can be obtained from dextran. The dextran used may be any suitable dextran; natural, synthetic or partially hydrolyzed. In an example, high molecular weight native dextran, i.e. dextran of a moleculer weight of more than $10^5$ kDa, can be used to provide oligodextran of a selected molecular weight. High molecular weight dextran can be obtained from micro-organisms, such as *Leuconostoc* spp. This process is well-known in the art. In essence, it encompasses the hydrolysis of high molecular weight native dextran to provide oligodextrans of different molecular weights. The hydrolyzed composition is fractionated to provide oligodextran fractions with different molecular weights, and the fractions are purified. Oligodextrans obtained by this process are well-known and commercially available.

In yet another embodiment, starch may be used as a starting material to prepare oligodextran. Starch is a cheap and easily accessible starting material. Potentially 100% may be converted to hydrolysis products, such as maltose syrups. In yet another embodiment, maltose syrup may be used as starting material to prepare oligodextran.

In another embodiment, the alpha-(1,6) oligodextran provided in step (1) for use in step (2) may be produced by micro-organisms capable of providing a glucan sucrase. The action of a glucan sucrase on a sucrose substrate provides a polymer typically with a molecular weight above $10^5$ kDa.

In yet another embodiment, oligodextran provided in step (1) for use in step (2) can be obtained by a synthesis process, which directly provides an oligodextran of desired molecular weight. For example, this is feasible with modified micro-organisms, such as *Leuconostoc* spp., which can produce a modified dextran sucrase. Suitable dextran sucrases may include variants of dextransucrase DSR-S obtained as described in WO2007/091178, which is incorporated herein by reference. These glucan sucrase mutants synthesize controlled size dextrans from sucrose in one step.

Referring to the above methods, glucose-containing starting material may be used in step (1a) of the methods described above, which may include starch or another material such as dextran or maltose syrup. In a preferred embodiment, starch is used as a starting material in step (1a) of the above methods. Up to 100% thereof may be converted to hydrolysis products, such as maltose or maltose syrups. The transglucosylation reaction, catalyzed by a transglucosidase, converts maltose into isomaltooligosaccharides (IMOS) mainly with a degree of polymerization (DP) of 2 to 5, such as isomaltose, panose, isopanose and isomaltotriose.

In the above methods, the IMOS can be used as an acceptor together with sucrose and a glucan sucrase. This leads to the elongation of the IMOS. The backbone of the IMOS is extended with glucose units and an oligodextran is formed. The glucan sucrases used in this step catalyze preferentially the formation of alpha-(1,6) linkages.

Glucan sucrases that can be used in step (1b) of the present invention are known in the art and will not be disclosed in detail herein. Suitable examples are, for instance, glucan sucrases obtained from *Leuconostoc mesenteroides* B512F, *Leuconostoc mesenteroides* B1299, and/or from *Leuconostoc mesenteroides* B742.

In a particular embodiment of a method according to the invention, when maltose syrup is used as a starting material, it is preferably subjected to method steps (1a) and (1b) as defined herein.

Figure 10A:
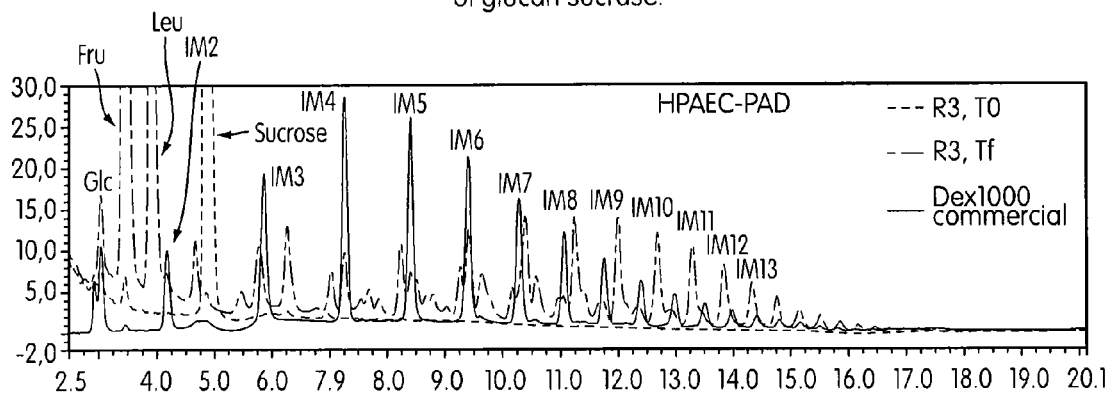
FIG. 10A illustrates addition of glucose to help obtain pure α1,6 structures of the present invention.
Figure 10A:
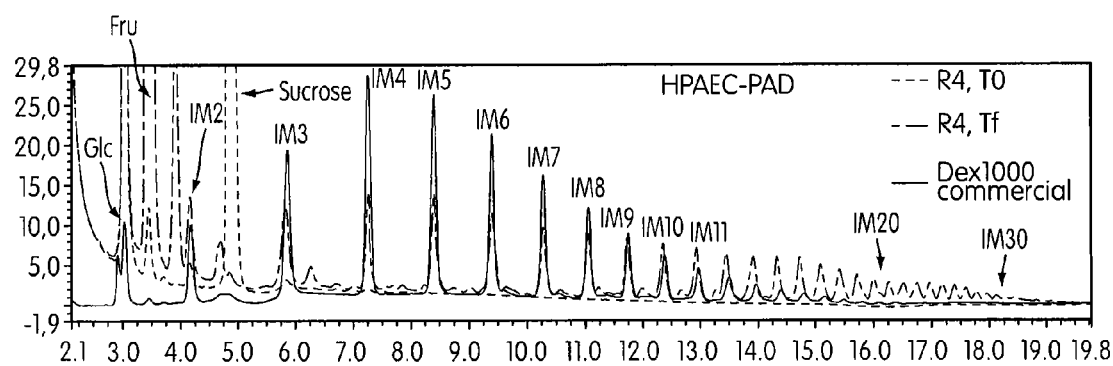

In another embodiment, step (1) comprises reacting sucrose with a glucan sucrase, whereby the alpha-(1,6) oligodextran is obtained. In a preferred embodiment, step (1) comprises reacting sucrose with a glucan sucrase in the presence of glucose, whereby the alpha-(1,6) oligodextran is obtained. Applicants have discovered that this permits direct synthesis of a desired backbone having a controlled molecular weight, i.e. centered on a specific MW value. Applicants have discovered that a backbone having a controlled size can be produced by adding to the sucrose a significant amount of glucose in the reaction medium. Thus, sucrose is the donor and glucose plays the role of acceptor (this reaction is called "synthesis by acceptor" reaction). The addition of glucose acceptor enhances the content of α-1,6 linkages in the structures, leading to a more pure IMOS type of product, i.e., addition of glucose helps to obtain pure α-1,6 structures (see FIG. 10A).

Figure 10B:
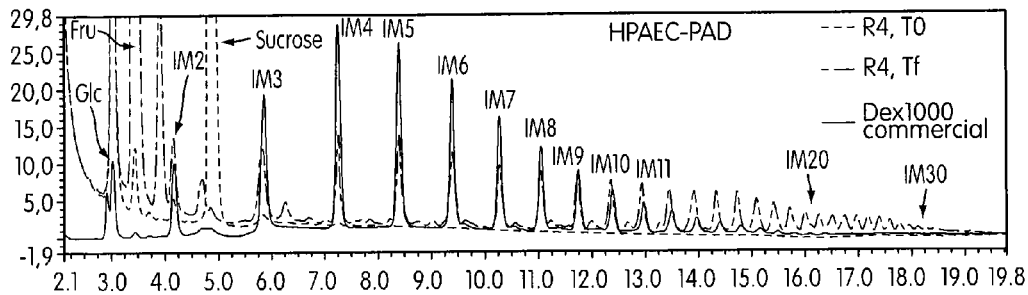
FIG. 10B illustrates that lowering the ratio of sucrose/glucose permits control of the polydispersity of the products.
Figure 10B:
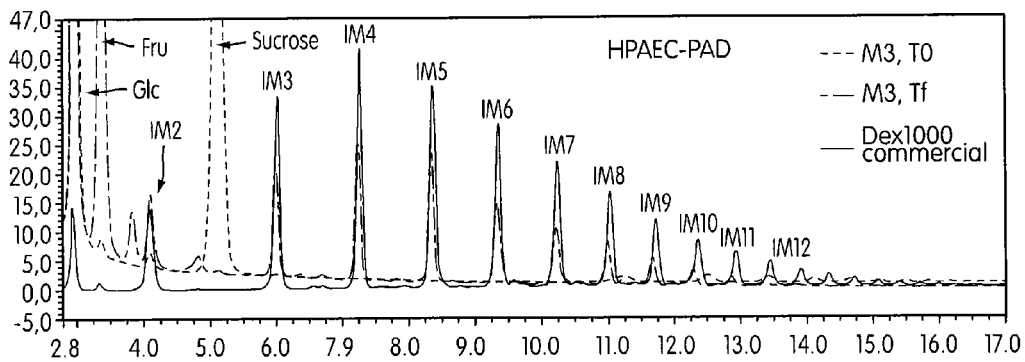
Figure 10B:
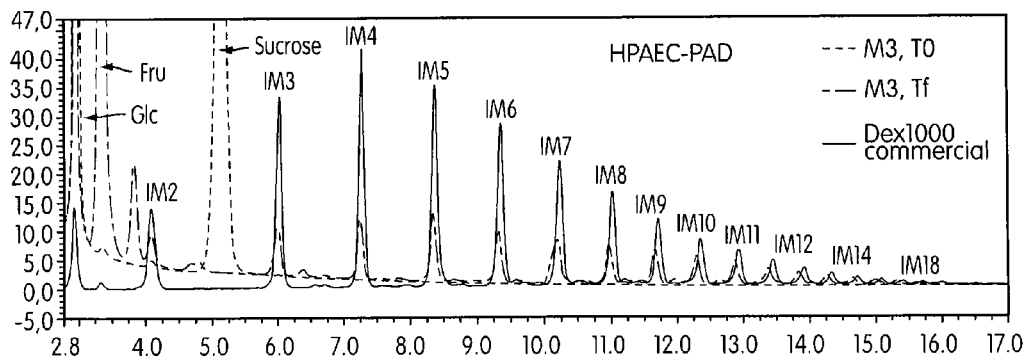
Figure 10C:
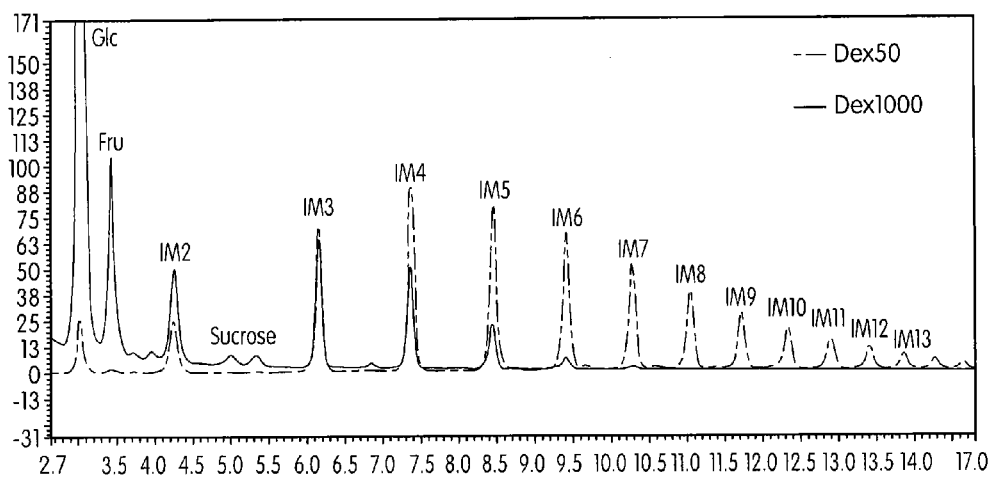
FIG. 10C illustrates that with the addition of glucose and adjustment of the ratio of sucrose:glucose, it is possible to control the synthesis of the desired compounds in terms of the distribution profile of DP and MW.
Figure 10C:
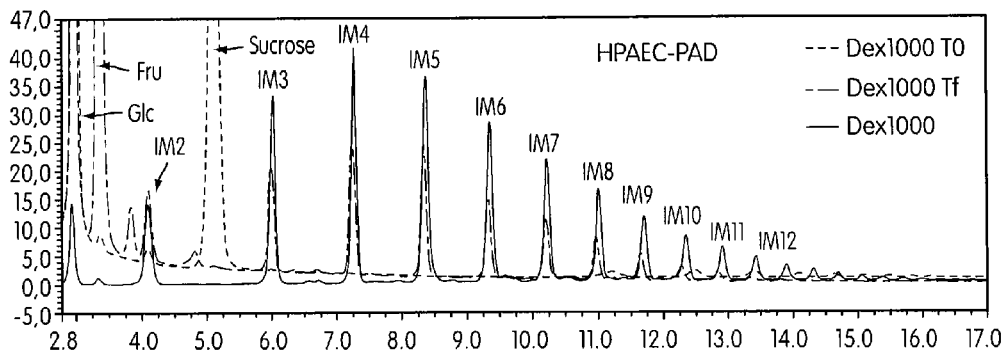

In another preferred embodiment, step (1) further comprises adjusting the ratio of sucrose:glucose, thereby adjusting the DP profile of the alpha-(1,6) oligodextran. Lowering the ratio of donor/acceptor permits control of the polydispersity of the products; for example, at a donor:acceptor ratio of 10, the degrees of polymerization are much higher, and by lowering the ratio down to 6 and then to 2, the synthesis of compounds having high degrees of polymerization is limited (see FIG. 10B). By adding glucose and adjusting the ratio of donor:acceptor, it is possible to control the synthesis of the desired compounds in terms of the distribution profile of DP and MW (see FIG. 10C).

In step (2), additional glucose units are attached to the oligosaccharide or oligodextran backbone. They are attached to the glucose units of the backbone in an alpha-(1,2)-position, so that alpha-(1,2)-branches are formed. The resulting compound is an alpha-(1,2)-branched alpha-(1,6) oligodextran. The branches are typically distributed randomly over the backbone.

In a preferred embodiment, a method according to the invention comprises a step wherein at least 15%, 20%, 25%, 30%, 35% or 40% of alpha-(1,2)-osidic side chains are introduced or grafted on the oligodextran backbone. This step advantageously allows the preparation process to yield a compound with a controlled digestibility and fermentability.

In a preferred embodiment, step (2) comprises introducing alpha-(1,2)-osidic side chains, preferably side chains of one or more glucopyranosyl (glucose) units, onto the alpha-(1,6) oligodextran with a suitable glucan sucrase in the presence of sucrose whereby alpha-(1,2)-branched alpha-(1,6) oligodextran is obtained. In this embodiment, step (2) comprises reacting the alpha-(1,6) oligodextran with a glucan sucrase (preferably transglucosidase GBD-CD2) in the presence of sucrose.

Glucan sucrases that can be used in step (2) of the present invention are known in the art and will not be disclosed in detail herein. In one example, a suitable glucan sucrase is dextransucrase DSR-E produced by the native *L. mesenteroides* NRRL B-1299 strain. In another example, suitable glucan sucrases for use in step (2) are described in WO 02/074943, FR2822162 and FR 2822163, which are incorporated herein by reference, and preferably include the glucan sucrases DSR-E and/or GBD-CD2. Generally, a glucan sucrase produced by the B-1299 strain, or GBD-CD2, can generate alpha 1,2 linkages Applicants found that the affinity of glucan sucrase for structures with one or repeated sequences of alpha-(1,6)-glucose moieties is higher than for maltose. Consequently, a reaction in step (2) using IMOS instead of maltose is improved in terms of time and yield.

In another embodiment, the invention provides a method wherein the degree of branching of the compounds, preferably a branching degree of at least 10% up to 40%, can be controlled by adjusting the ratio of acceptor/sucrose, in particular the ratio of IMOS to sucrose applied in step (2). Therefore, in another embodiment, the invention relates to a method wherein the ratio of IMOS to sucrose applied in step (2) is adjusted.

In an example, synthesis of alpha-(1,2)-branched alpha-(1, 6) oligodextran compounds according to the invention is obtained with the use of the transglucosidase GBD-CD2. With the use of this enzyme, controlled amounts of alpha-(1, 2)-branching can be obtained. GBD-CD2 is an alpha-(1,2) transglucosidase engineered from DSR-E, a glucan sucrase naturally produced by *Leuconostoc mesenteroides* NRRL B-1299. This enzyme catalyses, from sucrose, the alpha-(1, 2)-transglucosylation of glycosyl moieties onto alpha-1,6 dextran chains. Hydrolysis and transglucosylation may occur at an early stage of the process in the presence of sucrose and oligodextran as acceptor, wherein the oligodextran resulting from step (1) may be of a selected molecular weight. Applicants found that the amount of the synthesized alpha-(1,2) branches, or degree of branching, was found to be dependent on the ratio of sucrose applied in step (2) to alpha-(1,6) oligodextran. Alpha-(1,2)-branched alpha-(1,6) oligodextrans with controlled molecular weight and with controlled degree of branching can be obtained by adjusting the ratio of sucrose used in step (2) to oligodextran. In an example, the degree of branching could be varied from 13 to 40%. As illustrated in the examples below, in a preferred embodiment, the molar ratio of sucrose:alpha-(1,6) oligodextran is between about 0.10 and 5.00 and the percentage of alpha-(1,2) linkages (i.e., degree of branching) is between about 10% and 50%; more preferably, the molar ratio of sucrose:alpha-(1,6) oligodextran is between about 0.90 and 1.00 and the percentage of alpha-(1,2) linkages (i.e., degree of branching) is between about 30% and 40%.

The ability to use in step (1) an enzyme that can directly synthesize an oligodextran of desired molecular weight followed by the use in step (2) of an enzyme that can introduce a desired amount of alpha-(1,2) branching on a linear backbone is advantageous, as it results in a library of alpha-(1,2)-branched alpha-(1,6) oligodextran compounds that are tailored to specific needs, e.g. targeting a particular performance or use.

In an example, alpha-(1,2)-branched alpha-(1,6) oligodextrans are obtained from a process comprising step (1) using a variant of dextransucrase DSR-S as described in WO2007/091178, which is incorporated herein by reference, followed by step (2) using as enzyme GBD-CD2, as described in WO 02/074943 which is incorporated herein by reference.

Optionally, a method according to the present invention further comprises a purification step, in order to remove unwanted co-products. The optional purification step may comprise purifying the alpha-(1,2)-branched alpha-(1,6) oligodextran by filtration, wherein the purified oligodextran has an average molecular weight between about 0.5 and 100 kDa. Removal of fructose from the reaction medium can be based on existing state of the art technology. For instance, ultrafiltration can be used to isolate compounds centered on 70 kDa, and enrichment by chromatography on any type of resins used for separation can be used for the isolation of the 0.5 and/or 1 and/or 10 kDa alpha-(1,2)-branched alpha-(1,6) oligodextrans. Ion exchange resins may be used, such as cationic resins where calcium and/or potassium are the exchangeable counter ion.

In another aspect, the present invention provides compositions comprising branched oligodextran compounds as described herein. With a method as described above, both the amount of alpha-(1,2)-linkages and the molecular mass of branched oligodextrans can be controlled. This is advantageous for tailor-made production of alpha-(1,2)-branched alpha-(1,6) oligodextrans. A large panel of alpha-(1,2)-branched alpha-(1,6) oligodextran compounds can be synthesized by applying the herein described processes, opening the way to novel compositions.

As described in more detail below, another aspect of the invention provides a method for improving the health of a subject comprising administering a composition comprising an alpha-(1,2)-branched alpha-(1,6) oligodextran to a subject in an amount effective to exert a beneficial effect on the health of said subject. In one embodiment, the oligodextran is a prebiotic compound which provides a beneficial effect on the intestinal microflora of the subject. The beneficial effect of the oligodextrans of the present invention may comprise, for example, improving gut health, providing an analgesic effect (e.g., improving intestinal comfort), reducing lipid content (i.e., fat mass), affecting weight (e.g., weight gain), or preventing or treating a gastrointestinal disorder, diabetes, or symptoms thereof.

Examples of such beneficial effects include increased production of short chain fatty acids, decreased gas formation in the gastrointestinal tract, stimulated growth or activity of beneficial gut bacteria such as Bifidobacteria, gut pain relief, and combinations thereof. Another beneficial effect of oligodextrans of the present invention may comprise, for example, preventing or treating a cholesterol-related disorder or symptoms thereof. Examples of such beneficial effects include increased production of proprionate, decreased blood triglyceride levels, decreased low density lipoprotein levels, and combinations thereof.

In one aspect of the invention, the composition further comprises a probiotic organism, such as, for example, *Lactobacillus, Bifidobacterium, Enterococcus, Escherichia, Streptococcus, Saccharomyces*, and combinations thereof. In another aspect of the invention, the composition further comprises a dietary fiber, such as, for example, resistant maltodextrin, fiber dextrin, polydextrose, inulin, IMOS, the linear and branched dextrans, pullalan, hemicellulose, and combinations thereof.

A branched oligodextran compound as defined herein may be formulated into a suitable composition. The term "composition" in this context may include, for example, a nutritional or food composition, such as food products, food supplements, or functional foods. It may also include compositions for pharmaceutical use. The term "food" as used herein is intended to encompass food for human consumption as well as for animal consumption. By "functional food" it is meant any fresh or processed food claimed to have a health-promoting and/or disease-preventing and/or disease-reducing property beyond the basic nutritional function of supplying nutrients. Functional food may include, for example, processed food or foods fortified with health-promoting additives. Examples of functional food are foods fortified with vitamins, or fermented foods with live cultures.

A composition according to the invention may further contain other materials known in the art for inclusion in nutritional compositions, such as water or other aqueous solutions, fats, sugars, starch, binders, thickeners, colorants, flavorants, odorants, acidulants (such as lactic acid or malic acid, among others), stabilizers, or high intensity sweeteners, or minerals, among others. Examples of suitable food products include bread, breakfast cerials, biscuits, cakes, cookies, crackers, yogurt, kefir, miso, natto, tempeh, kimchee, sauerkraut, water, milk, fruit juice, vegetable juice, carbonated soft drinks, non-carbonated soft drinks, coffee, tea, beer, wine, liquor, alcoholic drink, snacks, soups, frozen desserts, fried foods, pizza, pasta products, potato products, rice products, corn products, wheat products, dairy products, hard candies, nutritional bars, cereals, dough, processed meats and cheeses, yoghurts, ice cream confections, milk-based drinks, salad dressings, sauces, toppings, desserts, confectionery products, cereal-based snack bars, prepared dishes, and the like.

Compositions according to the invention may also contain other dietary fibers as desired. For example, compositions may contain other polysaccharides such as insoluble and soluble fibers. By "dietary fiber" it is generally meant the substantially indigestible portion of plant foods that moves food through the digestive system, absorbing water and easing defecation, including both synthetically made fibers and those derived from plant or natural sources.

According to some definitions, "dietary fiber" refers to carbohydrate polymers having ten or more monomeric units (or in some cases carbohydrates having 3 to 9 monomeric units), which are not hydrolyzed by the endogenous enzymes in the small intestine of humans and which belong to the following categories: (1) edible carbohydrate polymers naturally occurring in food as consumed, or carbohydrate polymers that have been obtained from raw food material by physical, enzymatic, or chemical means, and that have been shown to have a health benefit as demonstrated by generally accepted scientific evidence, and/or (2) synthetic carbohydrate polymers which have been shown to have a health benefit as demonstrated by generally accepted scientific evidence.

Dietary fiber may consist of non-starch polysaccharides such as cellulose and many other plant components such as dextrins, inulin, lignin, chitins, pectins, beta-glucans, fructo-oligosaccharides, resistant starches, soluble corn (gluco) fiber, polydextrose, and gums such as guar, locust bean, xanthan or pullulan gum. Some dietary fibers are known to have a beneficial effect upon cholesterol and glucose levels. Suitable sources of soluble and insoluble fibers are commercially available.

An example of a suitable fiber is inulin or its hydrolysis products. The inulin may be provided in the form of a natural extract, which is suitable for human consumption. Suitable inulin extracts may be obtained from Orafti NV, Belgium under the trade mark "Raftiline." For example, the inulin may be provided in the form of Raftiline™ ST which is a fine white powder which contains about 90 to about 94% by weight of inulin, up to about 4% by weight of glucose and fructose, and about 4 to 9% by weight of sucrose. The average degree of polymerization of the inulin is about 10 to about 12. The hydrolysis products of inulin are fructo-oligosaccharides in the form of fructose oligomers containing 1-kestose(GF2), nystose(GF3), and 1F-fructofuranosyl nystose(GF4), in which fructosyl units(F) are bound to sucrose (GF) via a beta-(2,1) linkage, respectively. The fructo-oligosaccharides may be obtained commercially, for example from Orafti NV, Belgium under the trade mark "Raftilose." In a preferred embodiment, inulin extract is obtained from Sensus. Preferable Sensus products include Frutafit®HD and Frutafit®TEX! Frutafit®HD is a shorter chain inulin (about 8-13 monomeric units) and Frutafit®TEX! is a longer chain inulin (>22 monomers). In the examples and figures, they are generally indicated by inulin (i.e., shorter chain) or inulin TEX (i.e., longer chain).

In a preferred embodiment, a composition according to the invention may comprise at least two fiber sources. In a more preferred embodiment, one fiber source is an alpha-(1,2)-branched alpha-(1,6) dextran of the invention and the second fiber source is an oligo- or polysaccharide, selected from the group consisting of resistant maltodextrin, polydextrose, soluble corn (gluco) fiber, fiber dextrin, pullulan, resistant starch, inulin, fructo-oligosaccharides, galacto-oligosaccharides, hemicellulose and fructose oligomer syrup or lactulose or any other prebiotic compounds (including prebiotic disaccharides such as lactulose and tagatose among others). A result of this combination of a fiber source with alpha-(1,2)-branched alpha-(1,6) oligodextran is that a prebiotic is supplied to a larger part of the gastro-intestinal tract of a subject so that the prebiotics are not only fermented in the first part of the small intestine but across the entire length of the colon. By changing the ratio of the different compounds, one can potentially target the site of fermentation from proximal, mid, to distal colon. Consequently, a beneficial effect is exerted on the intestinal microflora ecology of the subject across the length of the entire colon. If both soluble and insoluble fibers are used, the weight ratio of soluble fiber to insoluble fiber is preferably about 1:4 to about 4:1; more preferably about 1:1 to about 2:1.

When the nutritional composition is in the form of a food product or nutritional formula, the nutritional composition may contain a protein source, a lipid source and/or a carbohydrate source. These sources may be selected as desired and are well known in the art. Compositions according to the present invention may alternatively include a vitamin and mineral profile or high intensity/potency sweeteners. For example, sufficient vitamins and minerals may be provided to supply about 25% to about 250% of the recommended daily allowance of the vitamins and minerals per 1000 calories of the nutritional composition.

The compounds and compositions as defined herein can be used as prebiotics, or as "synbiotics" when used in combination with probiotics, as discussed below. By "prebiotic" it is meant a food ingredient that beneficially affects the subject by selectively stimulating the growth and/or activity of one or a limited number of bacteria in the gastro-intestinal tract, particularly the colon, and thus improves the health of the host. Examples of prebiotics include fructooligosaccharides, inulin, polydextrose, resistant starch, soluble corn (gluco) fiber, glucooligosaccharides and galactooligosaccharides, arabinoxylan-oligosaccharides, and lactulose.

In another embodiment, compositions according to the invention further comprise a probiotic organism. By "probiotic organism" it is meant living microbiological dietary supplements that provide beneficial effects to the subject through their function in the digestive tract. In order to be effective the probiotic micro-organisms must be able to survive the digestive conditions, and they must be able to colonize the gastrointestinal tract at least temporarily without any harm to the subject. Only certain strains of micro-organisms have these properties. Preferably, the probiotic organism is selected from the group comprising *Lactobacillus* spp., *Bifidobacterium* spp., *Bacillus* spp., *Enterococcus* spp., *Escherichia* spp., *Streptococcus* spp., and *Saccharomyces* spp. Specific organisms include, but are not limited to *Bacillus subtilis, Bacillus cereus, Bifidobacterium bificum, Bifidobacterium breve, Bifidobacterium infantis, Bifidobacterium lactis, Bifidobacterium longum, Bifidobacterium thermophilum, Enterococcus faecium, Enterococcus faecium, Lactobacillus acidophilus, Lactobacillus bulgaricus, Lactobacillus casei, Lactobacillus lactis, Lactobacillus plantarum, Lactobacillus reuteri, Lactobacillus rhamnosus, Streptococcus faecium, diacetilactus, Streptococcus mutans, Streptococcus thermophilus, Saccharomyces boulardii, Torulopsia, Aspergillus oryzae,* and *Streptomyces* among others, including their vegetative spores, non-vegetative spores (*Bacillus*) and synthetic derivatives. More preferred probiotic micro-organisms according to the invention include, but are not limited to members of three bacterial genera: *Lactobacillus, Bifidobacterium* and *Saccharomyces*. In a preferred embodiment, the probiotic organism is *Bifidobacterium*.

The probiotic organism can be incorporated into the composition as a culture in water or another liquid or semisolid medium in which the probiotic remains viable. In another technique, a freeze-dried powder containing the probiotic organism may be incorporated into a particulate material or liquid or semisolid material by mixing or blending.

In a preferred embodiment, the composition comprises a probiotic organism in an amount of at least 1000 cells per 10 g, preferably 10,000 cells per 10 g, more preferably 100,000 cells per 10 g, most preferably 1,000,000 cells per 10 g. It will be understood that any reference to cell counts of a probiotic organism is to viable cells. Two or more probiotic organisms may be used in a composition.

Oligodextrans of the invention and compositions comprising them have a slow fermentability. This results in low and gradual amounts of gas produced and hence reduces symptoms related thereto. Inulin gives a boost of gas production which is rapid and high, whereas oligodextrans of the present invention give a gradual gas release which is lower than that of inulin. See, for example, Example 10 and FIGS. 8A and 8B. A rapid peak gives rise to gastrointestinal discomfort such as flatulence and bloating, whereas if gas production is gradual and low the body can more easily cope.

Based on in vitro digestion data (see, e.g., Example 4, FIGS. 4A and 4B, and Example 12), oligodextrans of the present invention are at least partially indigestible due to the alpha 1,2 branching. It is believed that the higher the level of branching, the better the compound resists digestion, and the larger the molecule, the lower the digestibility. Branching protects against digestion by human enzymes, and the larger the molecule, the lesser the fermentation speed (i.e., digestibility speed by bacteria) in the colon. Indigestibility is an important characteristic of fibers. Oligodextrans of the present invention can be classified as fibers based on this characteristic.

Use of compounds according to the invention permits the production of short chain fatty acids, particularly propionate. Propionate is known to lower cholesterol. Consequently, the compounds of the invention may lower the risk of developing high cholesterol. It was unexpected that the slow fermentability of oligodextrans below 100 kD stimulated the production of short chain fatty acids, especially proprionate, in fermentation studies. As the production of proprionate or the increased ratio of proprionate to acetate is beneficial for the control of cholesterol levels in a mammal in need thereof, the current invention is therefore of particular interest to nutritionists and consumers for the prevention and/or treatment of cardiovascular risks. Thus, another aspect of the invention provides a method for improving the health of a subject comprising administering a composition comprising an alpha-(1,2)-branched alpha-(1,6) oligodextran to a subject in an amount effective to exert a beneficial effect on the health of said subject, such as for treating cholesterol-related diseases. In addition, it is generally known that short chain fatty acids lower the pH in the gut and this helps calcium absorption. Thus, compounds according to the present invention may also affect mineral absorption. This means that they may also improve bone health, or prevent or treat osteoporosis by lowering the pH due to SCFA increases in the gut.

A "subject" is generally a human, although as will be appreciated by those skilled in the art, the subject may be a non-human animal. Thus, other subjects may include mammals, such as rodents (including mice, rats, hamsters and guinea pigs), cats, dogs, rabbits, cows, horses, goats, sheep, pigs, and primates (including monkeys, chimpanzees, orangutans and gorillas).

The term "cholesterol-related diseases" as used herein includes but is not limited to conditions which involve elevated levels of cholesterol, in particular non-high density lipid (non-HDL) cholesterol in plasma, e.g., elevated levels of LDL cholesterol and elevated HDL/LDL ratio, hypercholesterolemia, and hypertriglyceridemia, among others. In patients with hypercholesteremia, lowering of LDL cholesterol is among the primary targets of therapy. In patients with hypertriglyceridemia, lower high serum triglyceride concentrations are among the primary targets of therapy. In particular, the treatment of cholesterol-related diseases as defined herein comprises the control of blood cholesterol levels, blood triglyceride levels, blood lipoprotein levels, blood glucose, and insulin sensitivity by administering an alpha-(1,2)-branched alpha-(1,6) dextran according to the invention or a composition comprising an alpha-(1,2)-branched alpha-(1,6) dextran according to the invention.

An "effective amount" of a compound or composition as defined herein refers to an amount effective, at dosages and for periods of time necessary, to achieve a desired therapeutic result, such as lowering of blood cholesterol or preventing or treating a gastrointestinal disorder. For instance, the amount of a composition administered to a subject will vary depending upon factors such as the subject's condition, the subject's body weight, the age of the subject, and whether a composition is the sole source of nutrition. The effective amount may be readily set by a medical practitioner or dietician. In general, a sufficient amount of the composition is administered to provide the subject with up to about 40 g of dietary fiber (insoluble and soluble) per day; for example about 25 g to about 35 g of dietary fiber per day. The amount of alpha-(1,2)-branched alpha-(1,6) dextran that the subject receives is preferably in the range of about 0.1 g to about 15 g per day, or alternatively up to about 40 g per day. A compound or composition as defined herein may be taken in multiple doses, for example 2 to 5 times, spread out over the day or acutely, or may be taken in a single dose. A compound or composition as defined herein may also be fed continuously over a desired period. In certain embodiments, the desired period is at least one week or at least two weeks or at least three weeks or at least one month or at least six months.

In a preferred embodiment, the present invention provides a method for decreasing blood triglyceride levels in a subject in need thereof by administering a compound or a composition as defined herein to a subject in need thereof. In another preferred embodiment, the invention provides a method for decreasing low density lipoprotein levels in a subject in need thereof by administering a compound or a composition as defined herein to a subject in need thereof. In another preferred embodiment, the invention provides a method for increasing high density lipoprotein levels in a subject in need thereof by administering a compound or a composition as defined herein to a subject in need thereof.

In another aspect, the present invention provides an oligodextran having at least 15% alpha-(1,2)-osidic side chains. The presence of these alpha-(1-2) branches gives this oligodextran specific properties; in fact the human digestive system generally does not have the enzymatic means necessary for the hydrolysis of this type of bond. The presence of these branches provides partial or complete indigestibility to oligodextrans, and therefore virtually no or a slower absorption of glucose into the body, which results in a low glycemic response. Accordingly, the present invention provides oligodextrans as defined herein for the manufacture of food and drink compositions resulting in a low glycemic response. For example, these compounds can be used to replace sugar or other rapidly digestible carbohydrates, and thereby lower the glycemic load of foods, reduce calories, and/or lower the energy density of foods. Also, the stability of oligodextrans possessing this type of bond allows them to be easily passed through into the large intestine where they can serve as a substrate specific for the colonic microbial flora. These oligodextrans therefore possess characteristics as prebiotics.

In a further embodiment, compounds of the present invention are used for the treatment and/or improvement of gut health. The branched oligodextrans are fermented in the gut by the gut microflora and in an in vitro gut model show improved tolerance over inulin, i.e. the fermentation of the branched oligodextrans results in less gas production than inulin and lowers discomfort, such as flatulence and bloating, due to gas formation. Thus, the present invention also relates to a method for moderating gas formation in the gastrointestinal tract of a subject by administering a compound or a composition as defined herein to a subject in need thereof, so as to decrease gut pain or gut discomfort due to flatulence and bloating. In further embodiments, compositions of the present invention provide subjects with improved tolerance to food fermentation, and may be combined with fibers, such as inulin or FOS, GOS, or lactulose to improve tolerance by lowering gas production.

In a further embodiment, compounds of the present invention are administered in an amount effective to affect weight gain, such as by decreasing weight gain over time (see, e.g., example 9 below, in which rats treated with compounds according to the present invention exhibited less weight gain relative to control after 4 weeks of administration). This illustrates that compounds according to the invention affect weight gain and can be used to prevent or treat obesity or help in weight management. In addition, because it is generally known that some fibers, like inulin, can induce GLP1, compounds according to the present invention may also affect food intake, thereby leading to less weight gain (GLP1 has many known physiological functions, including decreasing food intake by increasing satiety and increasing insulin secretion from the pancreas). In another embodiment, compounds of the present invention are administered in an amount effective to decrease a subject's lipid content, i.e., by decreasing a subject's fat mass (see, e.g., example 11 below).

In further embodiments, compounds of the present invention may be administered to subjects in an amount effective to have any of the following effects: (1) anti-bacterial effects (by stimulating beneficial bacteria, oligodextrans may help to counteract the growth of pathogenic bacteria such as *Salmonella*); (2) effect on food intake and insulin sensitivity (and thus prevention or reduced risk of metabolic syndrome, diabetes, and/or obesity) by influencing GLP1 release and possibly other gut hormones involved in appetite regulation and insulin secretion; (3) effect on developmental programming by administering oligodextrans during pregnancy and/or breast feeding (this may influence the fetus and/or infant which results in prevention of insulin resistance/obesity later in life by influencing GLP1 and/or the gut flora (metabolites)); (4) calcium absorption by lowering pH due to SCFA production (fermentation); (5) since probiotics have been shown to affect autism, Alzheimer's, allergies, rheumatoid arthritis, among other immunological deficiencies, compounds according to the present invention may do the same, as all of these illnesses are at least partially due to inflammation, which can be counteracted by shifting the flora toward beneficial bacteria that lower local (gut) and systemic inflammation; (6) prevent or treat inflammatory bowel disease and/or irritable bowel syndrome, as administration of compounds according to the invention has been shown to ameliorate the inflammatory response in an animal model for Crohn's disease.

The invention is now further described with reference to the following examples.

EXAMPLES

Example 1

Table 1 illustrates embodiments of alpha-(1,2)-branched alpha-(1,6) compounds according to the invention having an average molecular weight between 1 and 70 kDa and having at least 15% alpha-(1,2)-osidic side chains.

TABLE 1

| Compound | Average Backbone Molecular weight (Da) | Degree of alpha-(1,2)-branching | Units in backbones | Units in branching | Total Units | Avg. MW of branched oligodextrans (Da) |
| --- | --- | --- | --- | --- | --- | --- |
| 1 | 1000 | 16% | 6.2 | 1.2 | 7.3 | 1190 |
| 2 | 1000 | 32% | 6.2 | 3.0 | 9.2 | 1493 |
| 3 | 6000 | 18% | 37.0 | 8.1 | 45.2 | 7317 |
| 4 | 6000 | 33% | 37.0 | 18.2 | 55.3 | 8955 |
| 5 | 40000 | 18% | 246.9 | 54.2 | 301.1 | 48780 |
| 6 | 40000 | 31% | 246.9 | 110.9 | 357.8 | 57971 |
| 7 | 70000 | 15% | 432.1 | 76.3 | 508.4 | 82353 |
| 8 | 70000 | 37% | 432.1 | 253.8 | 685.9 | 111111 |

The compounds listed in Table 1 can be obtained by carrying out a method according to the present invention, as disclosed herein.

As used in the examples below, F1 or DEX 1000-15 refers to Compound 1 in Table 1; F2 or DEX 1000-30 refers to Compound 2 in Table 1; and F3 or DEX 7000-30 refers to Compound 8 in Table 1.

Example 2

Table 2 illustrates an embodiment of a composition comprising an alpha-(1,2)-branched alpha-(1,6) oligodextran according to the invention.

TABLE 2

Enriched Flavored Water

| Ingredients: | g/100 ml |
| --- | --- |
| Sta Lite ® Polydextrose | 0.825 |
| Fructamyl 500 | 1.50 |
| Oligodextran | 1.00 |
| Citric Acid | 0.10 |
| Malic Acid | 0.10 |
| SPLENDA ® Sucralose | 0.006 |
| Strawberry flavour 78467-33 | 0.02 |
| Calcium Lacto Gluconate | 0.32 |
| Filtered Water | up to 100 ml |
| Total | 100 ml |

Example 3

This example illustrates the use of an alpha-(1,2)-branched alpha-(1,6) oligodextran compound according to the invention in a fermentation study. As demonstrated by the experiment described below, compounds of the invention induced the production of short chain fatty acids in the gastro-intestinal tract.

Fecal samples were obtained from 4 lean healthy male human volunteers (age 30-36 years) who were free of known metabolic and gastrointestinal diseases (e.g. diabetes, ulcerative colitis, Crohn's disease, irritable bowel syndrome, peptic ulcers and cancer). The samples were collected on site, kept in an anaerobic cabinet (10% $H_2$, 10% $CO_2$, 80% $N_2$) and used within a maximum of 15 minutes after collection. 1/10 w/v dilution in anaerobic PBS [0.1 mol/l phosphate buffer solution (pH 7.4)] was prepared and the samples homogenised in a stomacher for 2 minutes at normal speed. The test substances as represented by compounds of Table 1 were evaluated.

Ten sterile stirred batch culture fermentation systems (100 ml working volume) were set up, and aseptically filled with 45 ml basal medium (peptone water 2 g/l, yeast extract 2 g/l, NaCl 0.1 g/l, $K_2HPO_4$ 0.04 g/l, $KH_2PO_4$ 0.04 g/l, $MgSO_4.7H_2O$ 0.01 g/l, $CaCl_2.6H_2O$ 0.01, $NaHCO_3$ 2 g/l, Tween 80 2 ml Hemin 0.05 g/l, Vitamin $K_1$ 10 µl, Cysteine. HCl 0.5 g/l, Bile salts 0.5 g/l, pH7.0) and gassed overnight with oxygen free nitrogen. The carbohydrates (1/10 w/v) were added to the fermentation vessels just before the addition of the fecal slurry. The temperature was kept at 37° C. and the pH was controlled between 6.7 and 6.9 using an Electrolab pH controller. Each vessel was inoculated with 5 ml of fresh fecal slurry (1/10 w/v). The batch cultures were run over a period of 48 hours and 5 ml samples were obtained from each vessel at 0, 5, 10, 24, 36 and 48 h for fluorescent in situ hybridisation (FISH), and short chain fatty acid (SCFA) analysis.

Synthetic oligonucleotide probes targeting specific regions of the 16S rRNA molecule, labeled with the fluorescent dye Cy3, were utilized for the enumeration of *Bifidobacterium* genus (Bif164), *Bacteroides/Prevotella* (Bac303), *Lactobacillus/Enterococcus* (Lab158), and *C. perfringens, histolyticum* subgrp (Chis150) Variations of bacterial populations in human feces measured by fluorescent in situ hybridization with group specific 16S rRNA-targeted oligonucleotide probes. Labeled cells were visualized using fluorescent microscopy.

Three-hundred-twenty-five µl samples obtained from each vessel at each sampling time were fixed for 4 h (4° C.) in 1275 µl 4% (w/v) paraformaldehyde. Fixed cells were centrifuged at 15,000×G for 5 min and washed twice in 1 ml filtered sterilised PBS. The washed cells were re-suspended in 150 µl filtered PBS and stored in 150 µl ethanol (99%) at −20° C. for at least 1 h before further processing. Ten µl of the above samples were diluted in a suitable volume of PBS in order to obtain 20-100 fluorescent cells in each field of view and 20 µl of the above solution was added to each well of a 6 well teflon/poly-L-lysine coated slide (Tekdon Inc., Myakka City, USA). The samples were dried for 15 minutes in a drying chamber (46° C.). They were then dehydrated, using an alcohol series (50, 80 and 96% (v/v) ethanol) for 3 minutes in each solution. Slides were returned in the drying oven for 2 minutes to evaporate excess ethanol before adding the hybridization mixture.

Fifty µl of hybridization mixture (5 µl probe and 45 µl hybridisation buffer) was added to each well and left to hybridize for 4 hours in a microarray hybridization incubator. After hybridization slides were washed in 50 ml washing buffer for 15 minutes, they were dipped in cold water for a few seconds and dried with compressed air. Five µl of ProLong Gold antifade reagent was added onto each well and a coverslip was placed on each slide (20 mm coverslips). Slides were left overnight in the dark at room temperature prior to enumeration. Slides were examined under an epifluorescence microscope Nikon Eclipse 400 (Nikon, Surrey, UK) using the Fluor 100 lens. For each well 15 different fields of view were enumerated.

Bacterial counts were obtained using FISH. The groups enumerated for this report are for the main 4 numerically and functionally significant bacterial groups in human feces. Furthermore, of the samples collected over the 48 h fermentation period for FISH analysis only the 0, 10, 24 and 36 h samples were enumerated. Decisions on the duration of fermentation as well as timing of sample collection and selection of samples to be enumerated were based on a preliminary experiment investigating the rate of gas production in a non-pH controlled batch culture experiment which indicated that gas evolution started approximately at 9 h of fermentation and was mostly completed by 36 h of fermentation (results not presented here). Results are diagrammatically presented in FIG. 1 and FIG. 2.

From the bacterial groups enumerated and depicted in FIG. 1, it can be concluded that especially the 1 kDa branched oligodextrans are substrates exhibiting a good prebiotic potential, based on selective fermentation and bifidogenicity. They exhibited marked increases in bifidobacteria which were sustained after 24 h of batch culture fermentation and also gave a better bifidogenic effect as compared to a positive control (inulin TEX). As depicted in FIG. 2, fermentation of alpha-(1,2)-branched alpha-(1,6) dextran resulted in increased production of propionate, relative to acetate and absolutely.

The ratio of acetate to propionate of the illustrated compounds is as follows (see Table 3).

TABLE 3

| Sample | time point | ratio acetate/ propionate |
|---|---|---|
| oligodextran 1 kDa + 16% alpha-(1,2) | 10 h | 2.53 |
| | 24 h | 1.76 |
| | 36 h | 2.70 |
| | 48 h | 1.82 |
| oligodextran 1 kDa + 32% alpha-(1,2) | 10 h | 2.59 |
| | 24 h | 1.51 |
| | 36 h | 1.51 |
| | 48 h | 1.44 |
| oligodextran 6 kDa + 33% alpha-(1,2) | 10 h | 1.70 |
| | 24 h | 1.33 |
| | 36 h | 1.43 |
| | 48 h | 1.26 |
| oligodextran 70 kDa + 15% alpha-(1,2) | 10 h | 1.87 |
| | 24 h | 1.47 |
| | 36 h | 1.35 |
| | 48 h | 1.36 |
| oligodextran 70 kDa + 37% alpha-(1,2) | 10 h | 2.60 |
| | 24 h | 1.66 |
| | 36 h | 1.05 |
| | 48 h | 1.06 |
| Inulin TEX | 10 h | 2.65 |
| | 24 h | 2.16 |
| | 36 h | 2.13 |
| | 48 h | 2.24 |

FIG. 3 also illustrates acetate to propionate ratio (mM) in pH controlled batch culture fermentation.

Example 4

This example illustrates the use of an alpha-(1,2)-branched alpha-(1,6) oligodextran compound according to the invention in a degradability study. The method used for executing the degradability study is as described in Kendall et al., 2008 (*Effect of Novel Maize-based Dietary Fibers on Postprandial Glycemia and Insulinemia*, Kendall et al., Journal of the American College of Nutrition, Vol. 27, No. 6, 711-718, 2008.) Digestibility profiles of alpha-(1,2)-branched alpha-(1,6) oligodextran of controlled molecular weight (1 or 40 kDa) and controlled degree of branching (% branching: 0, 16, or 32%) were determined.

Figure 4A:
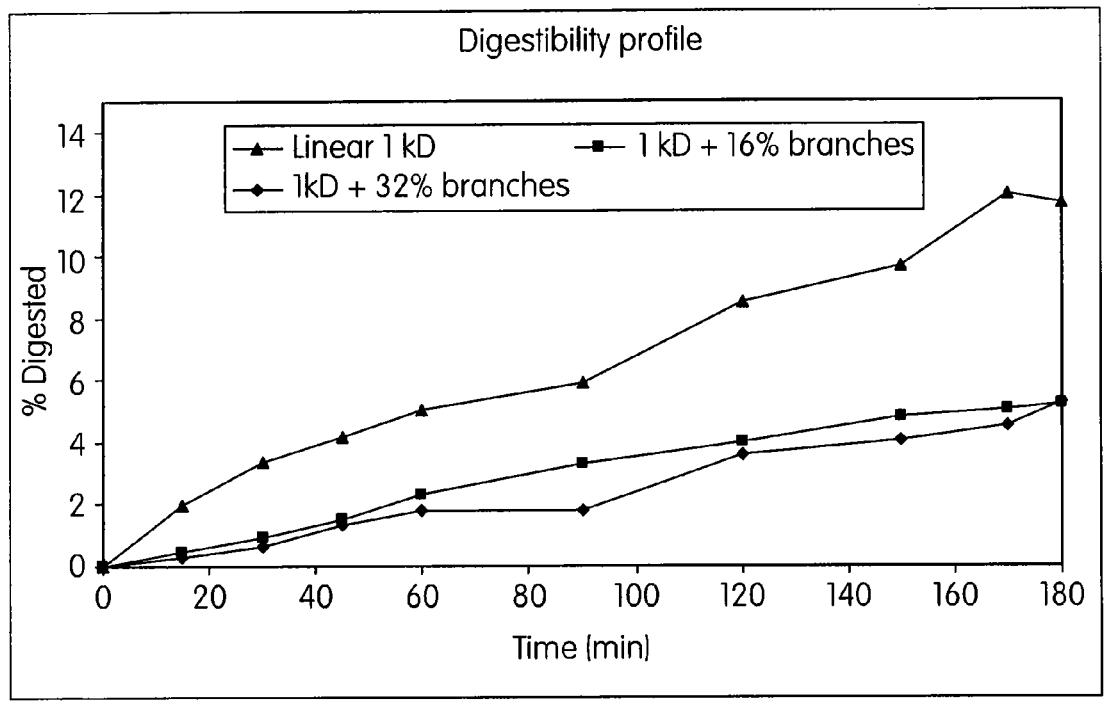
FIGS. 4A and 4B illustrate results of an in vitro digestion trial with compounds according to the invention. Diagrams representing digestibility profiles of alpha-(1,2)-branched alpha-(1,6) oligodextrans of controlled molecular weight (1 or 40 kDa) and controlled degree of branching (% branching: 0, 16 or 32%) are depicted.
Figure 4B:
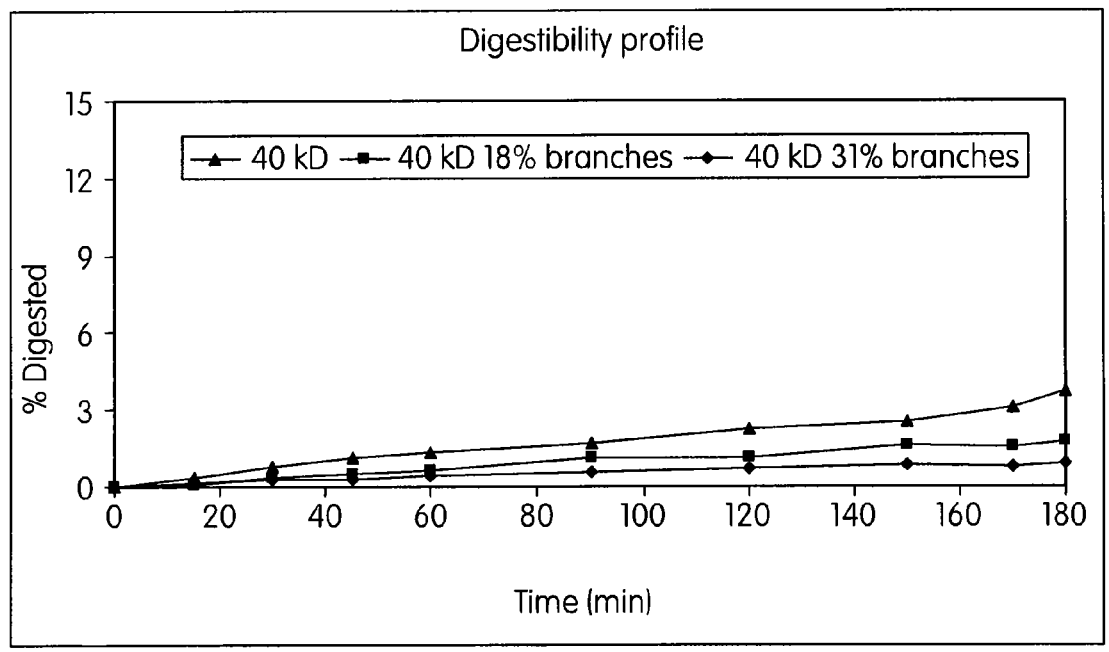

As depicted in FIGS. 4A and 4B, compounds according to the invention have decreased digestibility compared to compounds of the prior art. Decreased digestibility is advantageous as it provides a higher fiber content and/or higher prebiotic content. A further benefit is a lower dosage. The resistance to digestion is dependent on the length and the level of branching. For example, the 40 KD is less digestible than the 1 KD and the highly branched is less digestible than the non-branched molecules. Based on this in vitro digestion data, it may be concluded that oligodextrans of the present invention are at least partially indigestible due to the alpha 1,2 branching, as it is believed that the higher the level of branching, the better the compounds resist digestion, and the larger the compound, the lower the digestibility.

Example 5

This example relates to an in vitro study on the production of gas in fecal samples from human subjects provided with compounds of the invention compared to other control compounds such as inulin. Unless otherwise stated, all the reagents used were purchased from Sigma laboratories (Gillingham, Dorset, UK). Sterile glass tubes (18×150 mm, Bellco, Vineland, N.J., USA) containing 13.5 ml pre-reduced basal medium were placed in an anaerobic cabinet (10% $H_2$, 10% $CO_2$ and 80% $N_2$) and kept overnight. Test substrates (1/10 w/v) were added to the tubes prior to the addition of the fecal inocula (1/10 w/v). The tubes were then sealed with a gas impermeable butyl rubber septum (Supelco, Gillingham, Dorset, UK) and aluminium crimp (Supelco, Gillingham, Dorset, UK). Tubes were incubated at 37° C. under constant agitation.

Headspace pressure readings for each substrate were obtained every 3 h up to 36 h fermentation by inserting a sterile needle attached to a transducer into the butyl rubber septum of each tube. After each measurement, the headspace of each tube was allowed to equilibrate with atmosphere. The gas production experiments were performed in four replicates for each substrate. Quantification of gas volume (ml) was carried out using calibration curves of air pressure (PSI) by introducing air inside tubes with syringe of 0.5, 1, 1.5, 2, 3, 4, 5, 6 and 7 ml.

Figure 5:
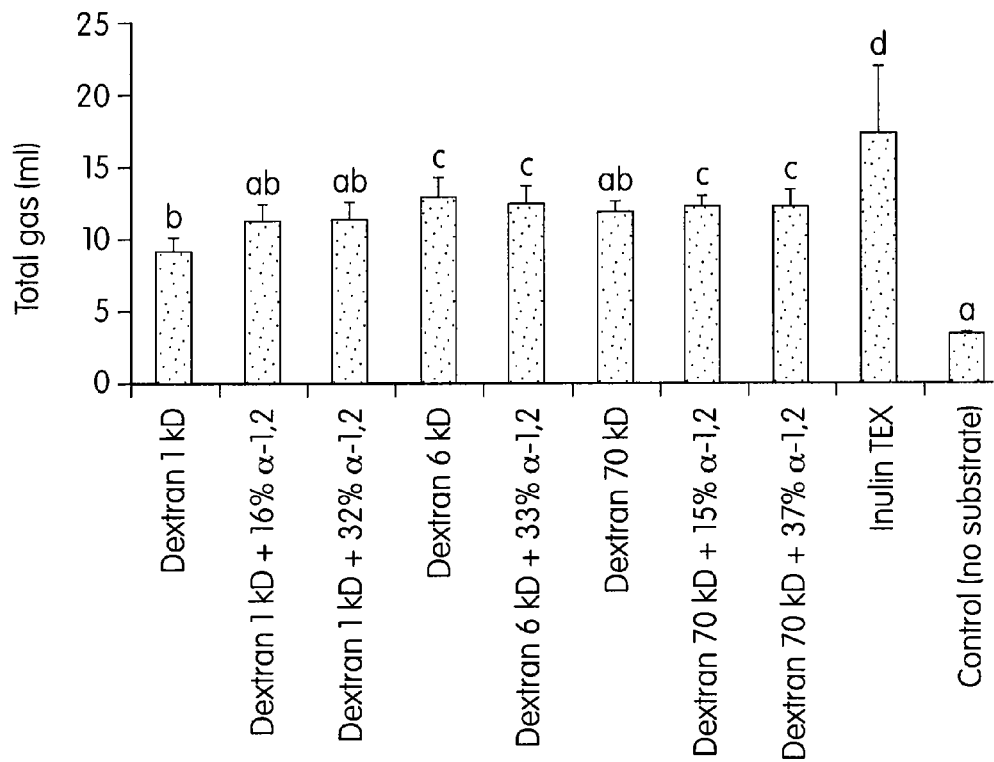
FIG. 5 illustrates diagrams representing results of a gas production trial with compounds according to the invention.

The resulting data and corresponding graphs are presented in FIG. 5 and Table 4. Branched oligodextrans of the present invention induced less gas production than the positive control inulin, suggesting that they are better tolerated than inulin. Therefore, use of these compounds is advantageous for fiber fortification of the human diet, especially for subjects sensitive to gas production in the bowel, e.g. for subjects suffering from constipation, irritable bowel syndrome or Crohn's disease (chronic inflammation of the colon). The compounds may also be beneficial to pets and other animals in this regard.

TABLE 4 gas production in donors provided with compounds of the present invention, and compounds of the prior art or in a control.

| Substrate | Average total gas (n = 4 donors, ml) | Standard deviation |
|---|---|---|
| 1 kDa + 16% α-1,2 | 10.99 | 1.27 |
| 1 kDa + 32% α-1,2 | 11.12 | 1.27 |
| 6 kDa + 33% α-1,2 | 12.18 | 1.26 |
| 70 kDa + 15% α-1,2 | 11.97 | 1.02 |
| 70 kDa + 37% α-1,2 | 11.96 | 1.19 |
| Inulin TEX | 16.89 | 4.19 |

TABLE 4-continued gas production in donors provided with compounds of the present invention, and compounds of the prior art or in a control.

| Substrate | Average total gas (n = 4 donors, ml) | Standard deviation |
|---|---|---|
| Inulin (Positive control) | 15.16 | 5.02 |
| Negative Control | 3.31 | 0.33 |

In addition, Table 5 below illustrates the rate of gas production expressed in ml/h over 36 h non-pH controlled batch culture fermentation (n=4).

TABLE 5

| Substrate | Rate of gas production (ml/h) |
|---|---|
| Dextran 1 kD | 0.616 |
| Dextran 1 kD + 16% α-1,2 | 0.563 |
| Dextran 1 kD + 32% α-1,2 | 0.552 |
| Dextran 6 kD | 0.621 |
| Dextran 6 kD + 33% α-1,2 | 0.492 |
| Dextran 70 kD | 0.551 |
| Dextran 70 kD + 15% α-1,2 | 0.529 |
| Dextran 70 kD + 37% α-1,2 | 0.453 |
| Inulin TEX | 1.082 |

Example 6

This example illustrates the synthesis of a range of branched oligodextran compounds of controlled molecular weight and degrees of branching according to the present invention. Several acceptor reactions have been carried out on linear oligodextrans of different MW as acceptors.

In a sterilized reactor, sucrose, oligodextran, and the enzyme GBD-CD2 were dissolved in distilled water and stirred. The pH was adjusted to 5.4 and the temperature regulated at 30° C. The reaction took place over 24 h under agitation and then the tank was heated up to 60° C. The acceptor reaction products were then filtered on cellulosic membranes with a cut off of 0.8 µm. The fructose was removed by applying the hot 1 kD and 6 kDa branched samples on ion exchange resin (Amberlite 1320K+) chromatography columns with water as mobile phase. The 40 and 70 kD samples were purified by diafiltration on Filtron membrane with 10 kD cut off. The samples were frozen and then freeze-dried in a lyophilisator using conventional methods. Different ratios of donor/acceptor i.e. sucrose/linear oligodextrans were incubated in the presence of a fixed amount of transglucosidase GBD-CD2. The different ratios are described in Table 5. The resulting compounds are listed above in Table 1.

TABLE 5

| Acceptor | Sucrose (g) | oligodextran acceptor (g) | Sucrose/(glucosyl units in oligodextran) in molar ratio | % alpha-(1,2) linkages | Resulting Compound (see Table 1) |
|---|---|---|---|---|---|
| 1 kD | 100 | 100 | 0.5 | 32 | 2 |
| 1 kD | 100 | 235 | 0.21 | 16 | 1 |
| 6 kD | 100 | 100 | 0.5 | 33 | 4 |
| 6 kD | 100 | 235 | 0.21 | 18 | 3 |
| 40 kD | 100 | 100 | 0.5 | 31 | 6 |
| 40 kD | 100 | 235 | 0.21 | 18 | 5 |
| 70 kD | 100 | 100 | 0.5 | 37 | 8 |
| 70 kD | 100 | 235 | 0.21 | 15 | 7 |

Example 7

Various amounts of alpha-1,6 oligodextrans of average molecular weight 70 kDa, obtained from *Leuconostoc mesenteroides* NRRL B-512F were incubated for 12 hours with sucrose (292 mM) and GBD-CD2 (1 U/ml) at 30° C. in sodium acetate buffer 20 mM (pH 5.4) supplemented with calcium chloride 3.4 mM. The amounts of alpha-1,6 dextran used were 62, 309, 463, 1235 and 2470 mM.

Oligodextran 10 kDa, 40 kDa, 70 kDa, and 2000 kDa were used at 300 mM concentration as described for the 70 kDa oligodextrans above. Sucrose depletion and glucose/fructose production were measured by HPLC. The branched oligodextrans obtained were precipitated with one volume of ethanol 95%, recovered by centrifugation, and washed three times with one volume of ultrapure water. This procedure was repeated once. Thereafter, the products obtained were freeze-dried. NMR-spectra were recorded to calculate the degree of alpha-(1,2) branching. 1H-NMR is preferred over 13C-NMR as it provides a higher signal/noise ratio for signals from anomeric protons of the pure alpha-(1,2)-branched alpha 1,6 oligodextrans.

The percentage of alpha-(1,2)-branching of the different oligodextrans produced was calculated from the relative intensities of the corresponding anomeric carbon or proton signals by integration of peak areas, as follows:

$$\% \text{ of alpha-}(1,2)\text{branching} = (100 \times (I_b + I_c)/2)/(I_a + I_b + I_c)$$

Ia,Ib,Ic are intensities of anomeric resonances. A is the anomeric resonance from "free carbon 2" alpha-1,6 linked D-Glc pyranosyl residues of the main linear chain. B is the anomeric resonance from alpha-1,6 linked D-Glc pyranosyl residues of the main linear chain, with the carbon 2 involved in an alpha-(1,2) linkage with a branched glucosyl unit. C is the anomeric resonance from alpha-(1,2)-linked D-Glc pyranosyl (i.e. branching points).

The initial molar [sucrose]/[oligodextran] ratio enabled the percentage of alpha-(1,2) branching in dextran to be controlled. At higher initial ratios, the formation of alpha-(1,2)

linkages decreased, a higher part of the glucosyl residues being transferred onto fructose to produce leucrose or released in the medium producing glucose (hydrolysis). Leucrose production increased at the end of the reaction due to high concentration of fructose in the medium.

The highest value of alpha-(1,2) linkages (40%) was observed for branched oligodextrans produced at an initial [sucrose]/[oligodextran] ratio of 4.74. The best compromise between a high percentage of alpha-(1,2) linkages and a low co-product yield is obtained for inital [sucrose]/[oligodextran] ratio of 0.63. Using this ratio, 69% of the glucosyl moieties of sucrose are transferred onto alpha 1,6 oligodextran leading to an alpha-(1,2) linkage degree of 35%.

The degree of alpha-(1,2)-linkages could be controlled by choosing the initial molar [sucrose]/[oligodextran] ratio used for the acceptor reaction. By varying the ratio from about 0.92 to about 4.74, alpha-(1,2)-branched alpha-(1,6) oligodextrans with degree of branching ranging from 10 to 40% were obtained.

Table 6 illustrates percentages of alpha-(1,2)-linkages determined by 1H-NMR and 13C-NMR for alpha-(1,2)-branched alpha-1,6-oligodextrans in the presence of 292 mM of sucrose and dextran of different molecular weights at concentrations ranging from 62 to 2470 mM (oligodextran concentrations expressed as glucosyl unit equivalents).

TABLE 6

| Molecular weight (kDa) | Polymerization degree (number of glucosyl units) | Initial molar [sucrose]/[oligodextran] ratio | % of alpha-(1,2) linkages (1H-NMR) | % of alpha-(1,2) linkages (13H-NMR) |
|---|---|---|---|---|
| 10 | 62 | 0.95 | 37.9 | 38.4 |
| 40 | 250 | 0.95 | 37.0 | 38.5 |
| 70 | 437 | 4.74 | 37.8 | 40.1 |
| 70 | 437 | 0.95 | 35.2 | 37.1 |
| 70 | 437 | 0.63 | 32.7 | 34.7 |
| 70 | 437 | 0.24 | 19.4 | 19.5 |
| 70 | 437 | 0.12 | 11.5 | 10.4 |
| 2000 | 12500 | 0.95 | 36.4 | 37.0 |

Example 8

Acceptor reactions in the presence of 10, 40, 70, or 2000 kDa oligodextran were performed at an initial [sucrose]/[oligodextran] ratio of 0.95. All the products showed similar alpha-(1,2) linkage content between 37 and 39% as determined by 13C-NMR. Surprisingly, the transglucosidase effect was the same no matter the molecular size of the acceptor, that is oligodextran from step (1). The molecular weight of the alpha-1,6-oligodextran obtained in step (1), and used in step (2) as acceptor, had no effect on the amount of alpha-(1,2)-linkages formed. The alpha-(1,2)-transglucosidase activity of GBD-CD2 was independent of the degree of polymerization of the product from step (1), at least for alpha 1,6 oligodextran with degree of polymerization (DP) ranging from 60 to 12500 glucosyl (glc) units.

Example 9

The analgesic properties and weight management effects of alpha-(1,2)-branched alpha-(1,6) oligodextrans were tested in healthy rats. The aim of this study was to evaluate in healthy rats whether alpha-(1,2)-branched alpha-(1,6) oligodextrans administered at two concentrations (1% and 5% of diet) for three weeks increased intestinal comfort and affected weight gain. In particular, colonic sensitivity was evaluated via a colorectal distension study and animals were weighed throughout the course of the experiment.

Male Sprague-Dawley rats (Charles River, l'Arbresle, France) weighing around 150 g are used in this study. Rats were maintained in laboratory conditions for 1 week before experiment. Animals were housed 5 per cage with food and water available ad libitum. Nociception in animals was assessed by measuring the intracolonic pressure required to induce a behavorial response during colorectal distension (CRD) due to the inflation of a balloon introduced in the colon. This response is characterized by an elevation of the hind part of the animal body and clearly visible abdominal contraction corresponding to the severe contractions. Briefly, rats were anesthetized with volatile anaesthesia (2% isoflurane), the balloon was inserted intrarectally in a minimally invasive manner to 7 cm from the anus, and the catheter was taped to the base of the tail. After 5 minutes, rats were placed in the middle of a 40×40-cm Plexiglas box and the catheter was connected to an electronic barostat apparatus (Distender Series IIR™, G& J Electronics). Increasing pressure was continuously applied until pain behavior was displayed or a cutoff pressure of 80 mm Hg was reached.

80 rats were tested:
10 rats control
10 rats+morphine (1 subcutaneous injection (1 mg/kg), 30 minutes before CRD assay)
10 rats+F1 1% (DEX1000-15)
10 rats+F1 5% (DEX1000-15)
10 rats+F2 1% (DEX1000-30)
10 rats+F2 5% (DEX1000-30)
10 rats+F3 1% (DEX7000-30)
10 rats+F3 5% (DEX7000-30)

As used herein, F1 or DEX 1000-15 refers to Compound 1 in Table 1. F2 or DEX 1000-30 refers to Compound 2 in Table 1. F3 or DEX 7000-30 refers to Compound 8 in Table 1. 1% or 5% refers to percentage of diet, as described below.

The quantity of each alpha-(1,2)-branched alpha-(1,6) oligodextran according to the invention administered by oral gavage once a day to rats was determined regarding to the theoretic diet consumption (food intake for rats 10 g/100 g of body weight). Each fiber was resuspended in 1 ml of drinking water.

5% correspond to 0.75 g of fiber/rat/day.
1% corresponds to 0.15 g of fiber/rat/day.

Figure 6A:
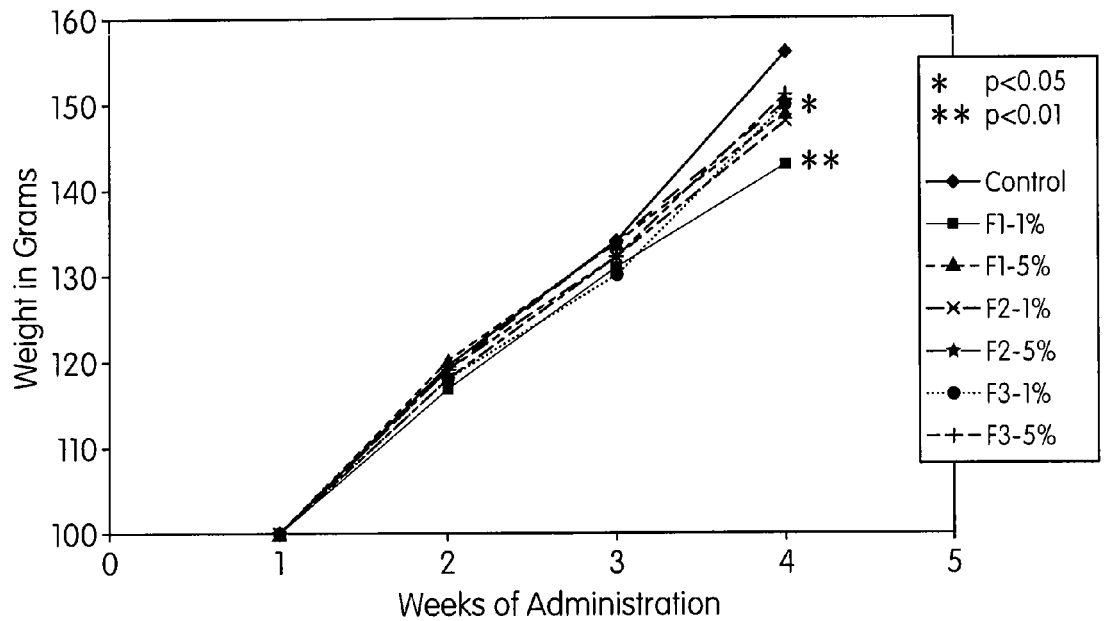
FIG. 6A illustrates the effect of compounds according to the present invention on rats' body weight gain during 4 weeks of administration.

The body weight of each rat was determined once a week during the 3 weeks of fiber administration (FIG. 6A). The evolution of fecal flora in rats before and after the 3 weeks of administration was determined using conventional bacterial methods of analysis using selective medium for bacterial growth.

FIG. 6A illustrates the evaluation of the rats body weight gain during 4 weeks fiber administration. It shows significant differences in body weight gain after 4 weeks in rats treated with F1 at 1 & 5% of the diet, F2 at 5% and F3 at 1% of the diet relative to control (water). Rats treated with oligodextrans according to the present invention exhibited less weight gain relative to control after 4 weeks of administration. This suggests that the oligodextrans may be administered to a subject in an amount effective to affect weight gain, such as by decreasing weight gain over time and thus help to manage weight.

Figure 6B:
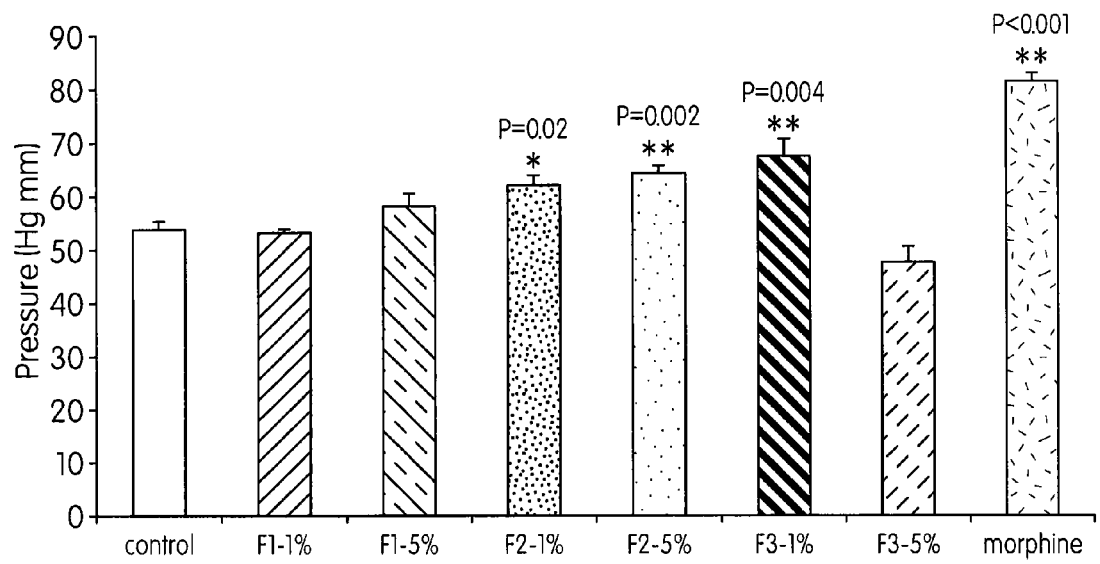
FIG. 6B illustrates the analgesic properties of compounds of the present invention according to the results of a colorectal distension study in rats.

FIG. 6B illustrates the analgesic properties of alpha-(1,2)-branched alpha-(1,6) oligodextrans according to the results of the colorectal distension study in rats. F2 (DEX 1000-30) at 1% and 5% and F3 (DEX 7000-30) at 1% have analgesic properties and improve the intestinal comfort in healthy rats.

Thus, compounds according to the present invention may be administered to a subject in an amount effective to provide an analgesic effect and/or improve intestinal comfort.

In addition, the effect of F1, F2, and F3 on intestinal microflora of the rats was evaluated after 4 weeks of treatment. The results are shown in FIG. 7. The tested products showed an increase in the number of *Lactobacilli*, when compared to the control, indicating that they exert prebiotic effects. The most efficient product was the DEX1000-30 at the dosage of 5%. With regard to pathogenic bacteria, DEX 1000-30 at 5% and DEX7000-30 at 5% showed a decrease in the number of *Enterococci* in the feces after 4 weeks of administration, when compared to the control. Thus, compounds according to the present invention may be administered to a subject in an amount effective to decrease pathogenic bacteria in the gut or intestines.

Overall, based on weight gain data, colorectal distension data, and data obtained in the study of fecal flora of treated animals, DEX 1000-30 (Compound 2 in Table 1 above) used at 5% was the most efficient product.

Example 10

In Example 3, the efficacy of oligodextrans according to the invention was evaluated in pH and temperature controlled batch culture experiments using fecal slurries from 4 lean healthy donors. This example provides the next step of the study, which involved the evaluation of the effect of a selection of the test substrates in vitro in identical experimental conditions as with the healthy lean donors but in this series of experiments slurries from 4 healthy obese donors were used. The aim was to identify possible differences in the composition of bacterial populations and their metabolic activities as well as their response to the selected substrates in the obese as compared to the lean donors.

Results from the lean batch cultures suggested that most fermentation is completed during the first 36 h of fermentation and that the obese experiments could be terminated at the 36 h time point. As the fermentation properties of this group were unknown, the cultures were run for 48 h.

Fecal samples were obtained from 4 obese healthy male human volunteers (age 44.5±5.74 years; BMI 37.7±3; waist circumference 125.9±9.86) who were free of known metabolic and gastrointestinal diseases (e.g. diabetes, ulcerative colitis, Crohn's disease, IBS, peptic ulcers and cancer). Samples were collected on site, kept in an anaerobic cabinet (10% $H_2$, 10% $CO_2$, 80% $N_2$) and used within a maximum of 15 minutes after collection. 1/10 w/v dilution in anaerobic PBS [0.1 mol/l phosphate buffer solution (pH 7.4)] was prepared and the samples homogenized in a stomacher for 2 minutes at normal speed.

The following highly pure prebiotics were evaluated:
Dextran 1 kDa, Dextran 1 kDa+16% α-1,2, Dextran 1 kDa+ 32% α-1,2, Dextran 6 kDa, Dextran 6 kDa+33% α-1,2 Dextran 70 kDa+15% α-1,2, Dextran 70 kDa, Dextran 70 kDa+37% α-1,2, and Inulin TEX (97%).

Sterile stirred batch culture fermentation systems (100 ml working volume) were set up, and aseptically filled with 45 ml basal medium (peptone water 2 g/l, yeast extract 2 g/l, NaCl 0.1 g/l, $K_2HPO_4$ 0.04 g/l, $KH_2PO_4$ 0.04 g/l, $MgSO_4.7H_2O$ 0.01 g/l, $CaCl_2.6H_2O$ 0.01, $NaHCO_3$ 2 g/l, Tween 80 2 ml, Hermin 0.05 g/l, Vitamin $K_1$ 10 µl, Cysteine. HCl 0.5 g/l, Bile salts 0.5 g/l, pH7.0) and gassed overnight with oxygen free nitrogen. The carbohydrates (1/10 w/v) were added to the fermentation vessels just before the addition of the faecal slurry. The temperature was kept at 37° C. and the pH was controlled between 6.7 and 6.9 using an Electrolab pH controller. Each vessel was inoculated with 5 ml of fresh faecal slurry (1/10 w/v). The batch cultures were run over a period of 48 hours and 5 ml samples were obtained from each vessel at 0, 10, 24, 36 and 48 h for FISH, and SCFA analysis.

Oligonucleotide probes. Synthetic oligonucleotide probes targeting specific regions of the 16S rRNA molecule, labeled with the fluorescent dye Cy3, were utilized for the enumeration of fecal bacteria. The Bif164 (*Bifidobacterium* genus) and Ato291 (*Atopobium* group) probes were used to enumerate most bacteria belonging to the *Actinobacteria* phylum.

A panel of probes was used to account for the majority of the *Firmicutes* phylum: *Lactobacillus/Enterococcus* (Lab158), *C. perfringens, histolyticum* subgrp (Chis150) *Clostridium* cluster IX (Prop853), *Ruminococcus* group (Rbro730/Rfla729), *Faecalibacterium prausnizii* group (Fpra655), and *E. rectale/C. coccoides* group (Erec482).

Finally, *Bacteroides/Prevotella* (Bac303), and the *Cytophaga-Flavobacter-Bacteroides* phylum (CFB719) were used to enumerate most *Bacteroidetes*.

Fluorescent in situ hybridisation (FISH). 325 µl samples obtained from each vessel at each sampling time were fixed for 4 h (4° C.) in 1275 µl 4% (w/v) paraformaldehyde. Fixed cells were centrifuged at 15,000×G for 5 min and washed twice in 1 ml filtered sterilised PBS. The washed cells were re-suspended in 150 µl filtered PBS and stored in 150 µl ethanol (99%) at −20° C. for at least 1 h before further processing.

Ten µl of the above samples were diluted in a suitable volume of PBS in order to obtain 20-100 fluorescent cells in each field of view and 20 µl of the above solution was added to each well of a 6 well teflon/poly-L-lysine coated slide (Tekdon Inc., Myakka City, USA). The samples were dried for 15 minutes in a drying chamber (46° C.). They were then dehydrated, using an alcohol series (50, 80 and 96% (v/v) ethanol) for 3 minutes in each solution. Slides were returned in the drying oven for 2 minutes to evaporate excess ethanol before adding the hybridization mixture.

Fifty µl of hybridization mixture (5 µl probe and 45 µl hybridisation buffer) was added to each well and left to hybridise for 4 hours in a microarray hybridisation incubator (Grant-Boekel, Cambridge, UK). After hybridization slides were washed in 50 ml washing buffer for 15 minutes. They were then dipped in cold water for a few seconds and dried with compressed air. 5 µl of ProLong Gold antifade reagent (Invitrogen Ltd., Paisley, UK) was added onto each well and a coverslip was placed on each slide (20 mm coverslips, thickness No1, VWR, Lutterworth, UK). Slides were left overnight in the dark at room temperature prior to enumeration. Slides were examined under an epifluorescence microscope Nikon Eclipse 400 (Nikon, Surrey, UK) using the Fluor 100 lens. For each well 15 different fields of view were enumerated.

Short chain fatty acid analyses were performed using ion exclusion high performance liquid chromatography (HPLC) system (LaChrom Merck Hitachi, Poole, Dorset UK) equipped with pump (L-7100), RI detector (L-7490) and autosampler (L-7200). Data was collected using Jones Chromatography Ltd. for Windows 2.0 software. The column used was an ion-exclusion Rezex ROA-Organic Acid H+ (8%), 300×7.80 mm (Phenomenex, Cheshire, UK). Guard columns were SecurityGuard™ Carbo-H+ 4×3.0 mm cartridges (Phenomenex, Cheshire, UK). The eluent used was 0.0025 mM sulphuric acids in HPLC-grade water.

Samples from each fermentation time point (1 ml) were centrifuged at 13,000×g for 10 min. Supernatants were filtered through a 0.22 µm filter unit (Millipore, Cork, Ireland).

20 μL was injected into the HPLC, operating at a flow rate of 0.5 ml/min with heated column at 84.2° C. The sample run time was 35 minutes. Sample quantification was carried out using calibration curves standard for lactate, acetate, propionate and butyrate, at concentrations of 12.5, 25, 50, 75 and 100 mM.

All probes were used to enumerate bacteria at 0, 10, 24 36 and 48 h with the exception of CFB719, Fpra655 and Rfla730/Rint729 for which the 48 h samples were not enumerated.

Figure 8A:
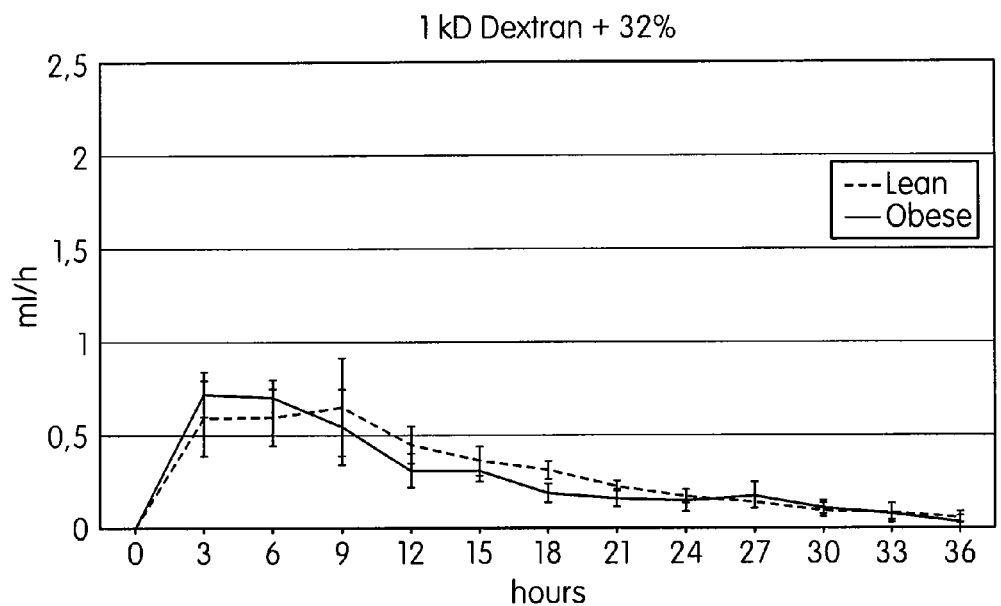
FIG. 8A illustrates the effect of compounds according to the present invention on rates of gas production in lean and obese donors.
Figure 8B:
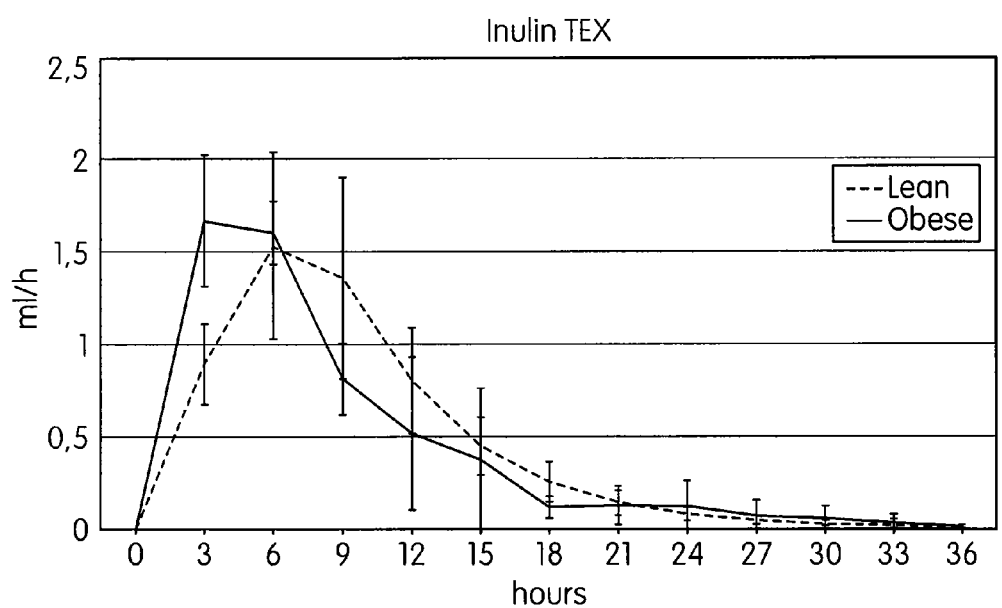
FIG. 8B illustrates the effect of inulin (used as a control) on rates of gas production in lean and obese donors.

Rates of gas production were very similar between lean and obese donors as were the patterns of rate of gas evolution, as can be seen in FIG. 8A, which provides a representative example of the oligodextrans of the present invention, as compared to inulin in FIG. 8B. The maximum rate of gas production observed for a specific substrate in the lean donor group was compared with the corresponding maximum rate from the obese donor group irrespective of time of occurrence. The total gas production did not differ between the lean and obese donors. However, it is clear that the test dextran causes less gas production, as well as more gradual gas production, in both lean and obese relative to inulin (FIGS. 8A and 8B). Thus, compounds according to the present invention may be administered to a subject in an amount effective to decrease gas production and/or cause slower gas production.

The lower molecular weight dextrans (1 kDa) exhibited the best bifidogenic effect. Significant increases were also observed with the 70 kDa dextran in the obese compared to baseline concentrations.

Figure 9A:
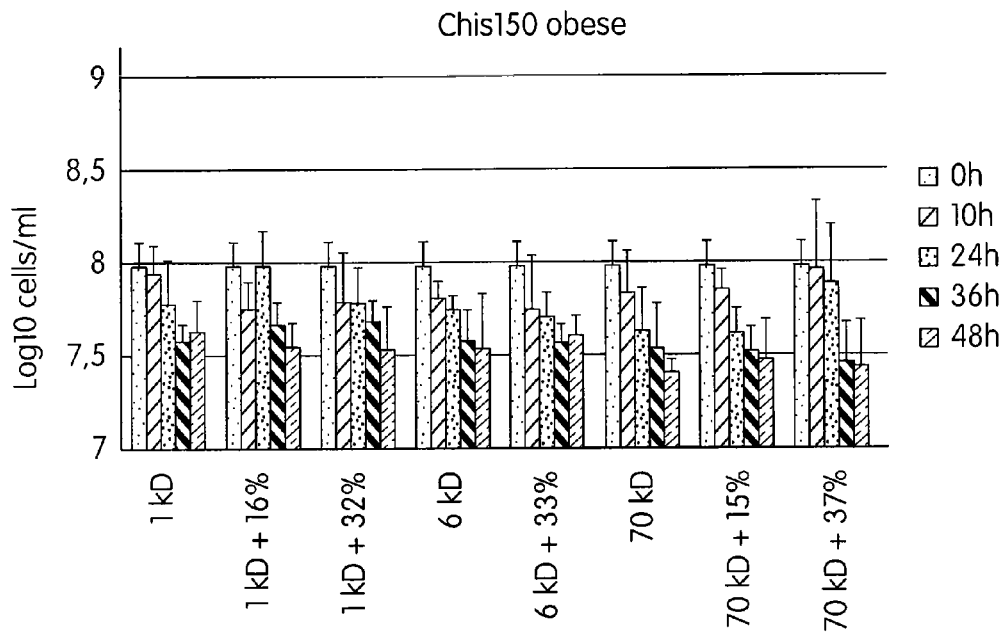
FIG. 9A illustrates levels of *C. histolyticum* following administration of compounds according to the present invention in obese donors.
Figure 9B:
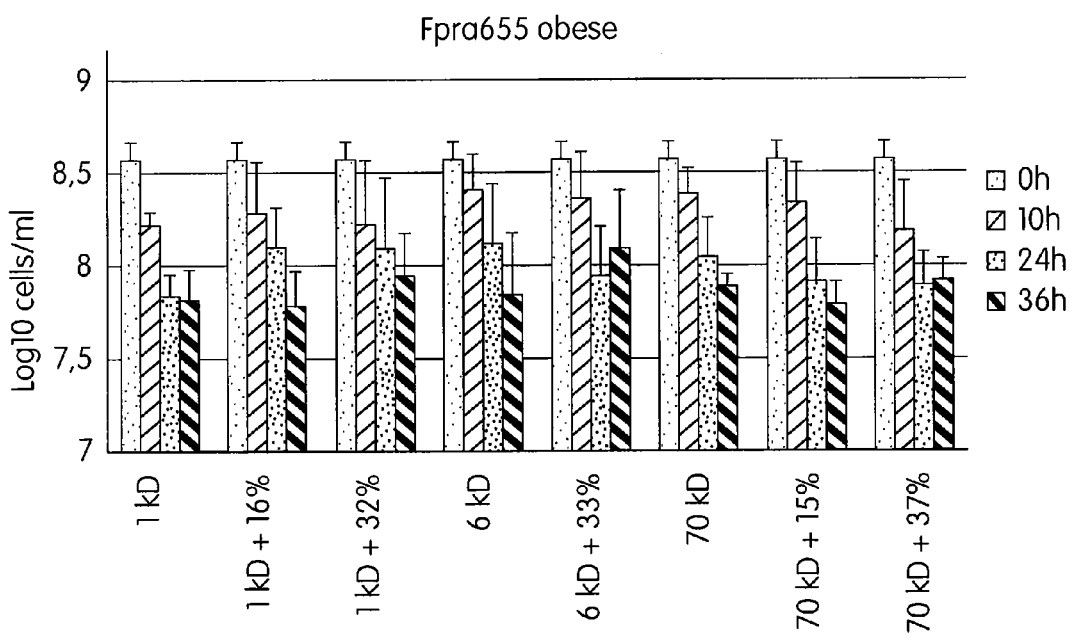
FIG. 9B illustrates levels of *F. prausnizii* following administration of compounds according to the present invention in obese donors.

Very interestingly, significant decreases were observed in the levels of the potential pathogen *C. histolyticum* with the dextrans in the obese donors (FIG. 9A) whereas trends were seen in the lean. Similar was the response in the *Ruminococcus* group. *F. prausnizii* decreased significantly with respect to baseline concentrations with all test substrates in the obese (FIG. 9B) and lean donors. Thus, compounds according to the present invention may be administered to a subject in an amount effective to decrease certain pathogenic bacteria in the gut or intestines.

SCFA production was similar in most cases between the two donor groups. We had observed that dextran fermentation in the lean donors resulted in the production of markedly high propionate levels with the exception of the linear, non-branched 1 kDa dextran. In the obese donor this was repeated with all dextrans apart from the 1 kDa but the ratios were even more in favor of propionate as smaller levels of acetate were produced during batch culture fermentation.

Overall in the obese donors the best performing substrates were the 1 kDa dextrans as they combined bifidogenicity with selectivity and negative effect on *C. histolyticum* levels. The branched 1 kDa dextrans may be superior as the acetate to propionate ratios achieved during batch culture fermentation were in favor of propionate, which may be of particular importance for obese individuals as this may mediate a hypo-cholesterolemic effect.

Example 11

Oligodextrans according to the present invention were evaluated for their effect on lipid content using the in vivo model *Caenorhabditis elegans*. The substrates evaluated were TLD-1000 (unbranched 1 kDa dextran) and TLD-1030 (1 kDa dextran+32% α-1,2). TLD-1000 was evaluated at five different concentrations (1%, 0.5%, 0.25%, 0.1%, 0.05%, 0.025%, and 0.01% w/v). A negative control (DMSO) and positive control (Orlistat) were also included. Each substrate was assayed four times with a total of 120 worms per substrate and concentration.

In the case of the TLD-1000 substrate, concentrations of 0.25% and 0.1% gave a substantial reduction in lipid content, but the optimal concentration was 0.1%, which achieved a reduction of 30%. For the highest assayed concentrations (1% and 0.5%) and the lowest concentration (0.05%), the reduction was around 10%. In the case of the TLD-1030 substrate, most of the assayed concentrations gave a substantial reduction in lipid content. At a low concentration (0.05%), it is possible to find maximum reduction in lipid content at values near 40%, a value lower than that obtained with the positive control Orlistat. These reductions in lipid content suggest that compounds of the present invention may be administered to a subject in an amount effect to decrease the subject's lipid content, i.e., reduce the subject's fat mass.

Overall, the optimal dosage for each substrate was different. This optimal dose was established at values of 0.1% and 0.05% for TLD-1000 and TLD-1030, respectively. The reduction in lipid content at the optimal concentration in every substrate is higher in TLD-1030.

Example 12

The caloric values of TLD1000 (linear 1 kDa oligodextran), TLD1030 (1 kDa 32% branched oligodextran), and TLD7030 (70 kDa 37% branched oligodextran), as described in Table 1, were determined in a rooster model.

The TME energy corrected to zero nitrogen balance (TME) of three compounds according to the invention were determined in caged cecectomized or conventional Single Comb White Leghorn roosters. Roosters were fasted for 24 hours and five roosters were then tube-fed (into crop) 30 g of test feed ingredient. The roosters were then placed in individual cages and a tray was placed under each cage and all excreta were collected for 24 hours. The excreta were then freeze dried, weighed, and ground and analyzed for gross energy and nitrogen. TMEn was then calculated using energy excretion by fasted roosters for an endogenous correction. The results were then statistically analyzed and summarized in Table 7 below.

TABLE 7

True Metabolizable Energy (TME) Evaluation of Oligodextrans

| Sample | Cage | Gross Energy as-is (kcal/g) | DryMatter (%) | $TME_n DM$ (kcal/g DM) | Average $TME_n DM$ (kcal/g DM) |
|---|---|---|---|---|---|
| TLD1000 | 405-151 | 3.733 | 93.0 | 3.845 | $3.650^a$ |
|  | 405-153 |  |  | 3.598 |  |
|  | 405-155 |  |  | 3.629 |  |
|  | 405-159 |  |  | 3.698 |  |
|  | 406-115 |  |  | 3.479 |  |
| TLD1030 | 405-161 | 3.917 | 98.7 | 1.005 | $0.745^c$ |
|  | 405-165 |  |  | 0.905 |  |
|  | 405-169 |  |  | 0.473 |  |
|  | 406-117 |  |  | 0.563 |  |
|  | 406-119 |  |  | 0.777 |  |
| TLD7030 | 405-173 | 3.527 | 98.2 | 0.298 | $0.136^d$ |
|  | 405-175 |  |  | -0.028 |  |
|  | 405-177 |  |  | 0.413 |  |
|  | 405-179 |  |  | 0.263 |  |
|  | 406-123 |  |  | -0.267 |  |

LSD = 0.2624
Pooled SEM = 0.0875
P < 0.0001

TLD1000 has a total metabolizable energy (TME) of 3.650 kcal/g, which means it was almost completely digested. The TME for TLD1030 was less than the TME of TLD1000, and the TME for TLD7030 was even less than the TME of TLD1030. This means that these products are generally not digestible in the small intestine, and also means that there is a difference in speed of fermentability in the colon among the oligodextrans. TLD7030 is hardly digested, nor fermented, according to the low TME value. The most important indicator from these data is that the linear oligodextran (TLD1000) is digestible and the branched oligodextrans (TLD1030 and TLD7030) are not. Thus, branching protects against digestion by human enzymes, and the longer the molecule, the lesser the fermentation speed (i.e., digestibility speed by bacteria) in the colon. Indigestibility is an important characteristic of fibers. Oligodextrans of the present invention can classify as fibers based on this characteristic.

Example 13

The study aims at identifying the effect of compounds according to the invention on metabolic markers in a high fat diet induced obesity model in mice after a 12 weeks treatment. The data represented below are showing the effect of the compounds on body weight, body weight gain, fasting glycemia, and after an OGTT (oral glucose tolerance test) assay following 6 weeks of treatment. As used herein, TLD1030 refers to 1 kDa+32% branched oligodextran; TLD1015 refers to 1 kDa+16% branched oligodextran; and TLD7030 refers to 70 kDa+37% branched oligodextran, as shown in Table 1 above.

Male C57BL/6j mice, purchased from Charles River, were housed with access to a standard chow diet and water ad libitum during a 2-weeks acclimatization period. After eleven days of acclimatization with D12450B diet, mice were randomized on body weight and divided in 4 groups of eight animals. Mice were then fed with High Fat Diet (D12492) alone, or with High fat containing 1% of product to be tested. Animals were individually weighed twice a week. Body weight gain was calculated by subtracting the final value obtained (second measure of a week) from the total body weight at day 0 of the study.

At week 6, a glucose tolerance test was performed. This approach helped to highlight the effect of different compounds on the insulin resistance induced by high fat diet. The mice were fasted the day before the test to 18 h. On the test day (9 am) mice were weighed and administered with glucose (2 g/kg-10 mL/kg a solution of 10% glucose) orally (per os). Their blood glucose was measured at time T0/T+15/+30/+60/T+90/T+120/180 min using a glucometer taking a drop of blood after incision tail vein of animal guards. Body weight, fasting glucose, and OGTT data differences between groups were calculated using a Student's t-test on Sigma Plot 11.0 (2008) Systat Software, Inc.

Figure 12A:
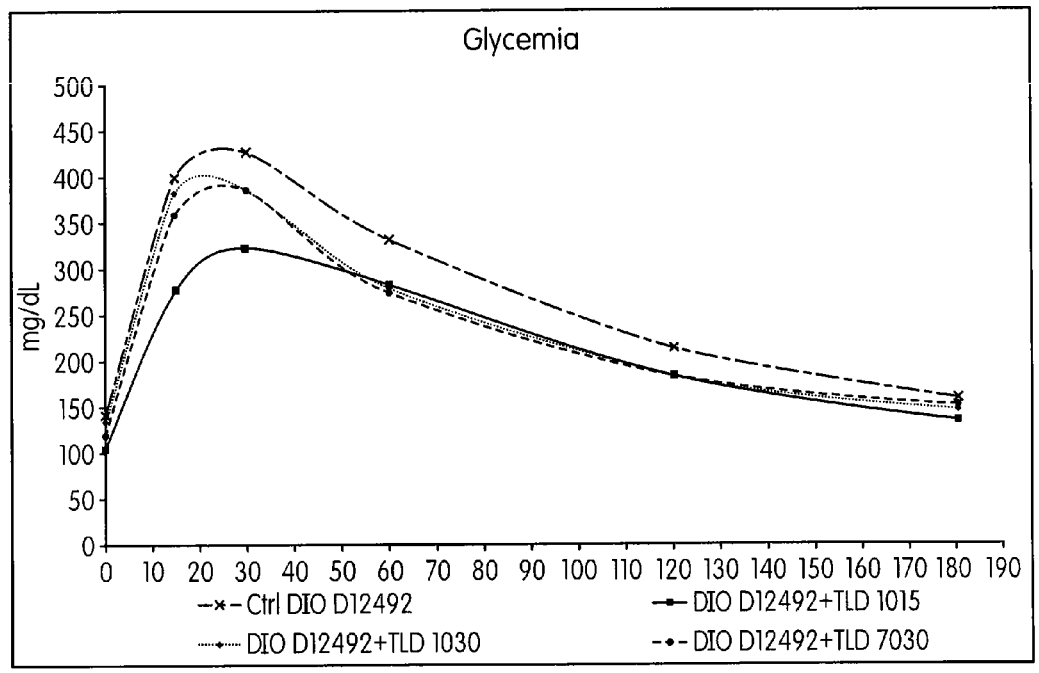
FIG. 12 illustrates glucose tolerance in rats following administration of compounds according to the present invention
Figure 12B:
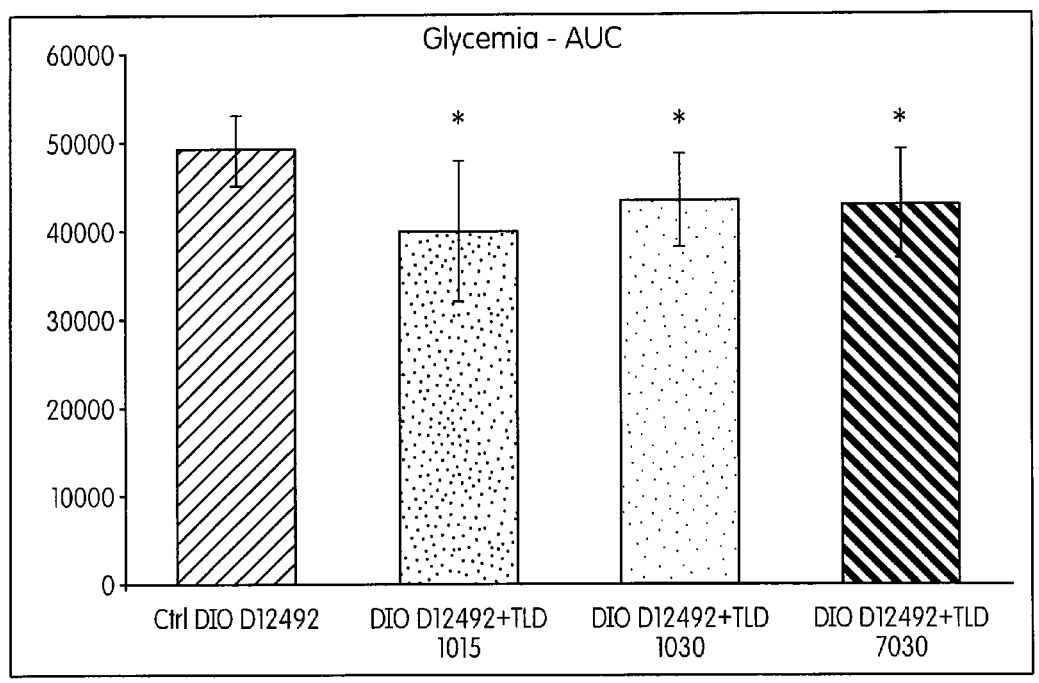

After 6 weeks of treatment, TLD1030 when compared to the DIO (=diet induced obesity) control showed a significant reduction in body weight gain (−9.68%), as shown in FIG. 11. FIG. 11 illustrates body weight gain (grams and % of day 1) and fasting glucose (mg/dl) mean value (+/−SEM). (*p≤0.05; p:≤0.01; *p:≤0.001 (t-test versus Ctrl DIO)). On the fasting glycemia parameter, a significant reduction (−19.5%) was observed with TLD1015. The OGTT data show that the three products were able to significantly decrease the glycemia AUC (FIG. 12 and Table 8).

These results suggest that compounds of the present invention may be administered to a subject in an amount effective to increase a subject's tolerance to glucose, increase insulin secretion, and reduce weight gain in a subject on a high fat or typically Western type diet.

TABLE 8

Area under the curve mean value (+/−SEM) 1 (week 6)

| Group | Area under the curve |
| --- | --- |
| DIO D12492 | 49190 ± 3979 |
| DIO D12492 + TLD 1015 | 40039 ± 7959* |
| DIO D12492 + TLD 1030 | 43468 ± 5248* |
| DIO D12492 + TLD 7030 | 43034 ± 6147* |

*p ≤ 0.05;
** p: ≤ 0.01;
***p: ≤ 0.001 (t-test versus Ctrl DIO)

Although illustrated and described above with reference to certain specific embodiments, the present invention is nevertheless not intended to be limited to the details shown. Rather, various modifications may be made in the details within the scope and range of equivalents of the claims and without departing from the invention.

What is claimed is:

1. A composition comprising an alpha-(1,2)-branched alpha-(1,6) oligodextran,
   wherein said oligodextran comprises a backbone comprising alpha-D-glucopyranosyl units linked by alpha-(1,6)-linkages,
   wherein said backbone has an average molecular weight between about 1 kDa and 10 kDa,
   wherein said oligodextran comprises between about 10% and 50% alpha-(1,2)osidic side chains,
   wherein the alpha-(1,2)-osidic side chains are randomly distributed over the backbone,
   whereby the composition is useful for improving the health of a subject.

2. The composition of claim 1, wherein said oligodextran is a prebiotic compound.

3. The composition of claim 1, wherein said backbone comprises at least 90% alpha-(1,6)-D-glucopyranosidic linkages.

4. The composition of claim 1, wherein said oligodextran comprises less than 10% alpha-(1,4)-linkages.

* * * * *